US011185551B2

(12) United States Patent
Hartrick

(10) Patent No.: US 11,185,551 B2
(45) Date of Patent: Nov. 30, 2021

(54) PERIPHERALLY-RESTRICTED DUAL-ACTING KAPPA AND DELTA OPIOID AGONIST FOR ANALGESIA IN PAIN STATES INVOLVING THE INFLAMMATORY RESPONSE

(71) Applicant: Caventure Drug Discovery, Inc., Bloomfield Hills, MI (US)

(72) Inventor: Craig Hartrick, Bloomfield Hills, MI (US)

(73) Assignee: Caventure Drug Discovery, Inc., Bloomfield Hills, MI (US)

( * ) Notice: Subject to any disclaimer, the term of this patent is extended or adjusted under 35 U.S.C. 154(b) by 0 days.

(21) Appl. No.: 16/066,184

(22) PCT Filed: Jun. 22, 2018

(86) PCT No.: PCT/US2018/038936
§ 371 (c)(1),
(2) Date: Jun. 26, 2018

(87) PCT Pub. No.: WO2019/010014
PCT Pub. Date: Jan. 10, 2019

(65) Prior Publication Data
US 2021/0161912 A1  Jun. 3, 2021

Related U.S. Application Data

(60) Provisional application No. 62/529,285, filed on Jul. 6, 2017.

(51) Int. Cl.
*A61P 29/00* (2006.01)
*A61K 31/4188* (2006.01)
*A61K 31/5517* (2006.01)
*C07D 403/14* (2006.01)

(52) U.S. Cl.
CPC .......... *A61K 31/5517* (2013.01); *A61P 29/00* (2018.01); *A61K 31/4188* (2013.01); *C07D 403/14* (2013.01)

(58) Field of Classification Search
CPC ............ A61K 31/5517; A61K 31/4188; A61P 29/00; C07D 491/00; C07D 403/14
See application file for complete search history.

(56) References Cited

U.S. PATENT DOCUMENTS

| 5,800,385 A | 9/1998 | Demopulos et al. |
| 2003/0008807 A1 | 1/2003 | Levine et al. |
| 2005/0152905 A1 | 7/2005 | Omoigui |
| 2017/0007610 A1 | 1/2017 | Desai et al. |

OTHER PUBLICATIONS

Austin, P. J. et al., "The neuro-immune balance in neuropathic pain: Involvement of inflammatory immune cells, immune-like glial cells and cytokines," *J. Neuroimmunology* 2010; 229: 26-50.
Barber, A. et al., "Central and peripheral actions of the novel kappa-opioid receptor agonist, EMD 60400," *Br. J. Pharmacol.*, 1994; 111: 843-851.
Bee, L. A. et al., "Mu-opioid and noradrenergic a(2)-adrenoceptor contributions to the effects of tapentadol on spinal electrophysiological measures of nociception in nerve-injured rats," *Pain*, 2011; 152(1): 131-139.
Berg, K. A. et al., "Allosteric Interactions between δ and κ Opioid Receptors in Peripheral Sensory Neurons," *Mol Pharmacol.*, 2012; 81: 264-272.
Brackley, A. D. et al., "GRK2 Constitutively Governs Peripheral Delta Opioid Receptor Activity," *Cell Reports*, 2016; 16(10): 2686-2698.
Craft, R. M. et al., "Opioid antinociception in a rat model of visceral pain: systemic versus local drug administration," *Journal of Pharmacology and Experimental Therapeutics*, Dec. 1995; 275(3): 1535-1542.
Eans, S. O. et al., "Parallel Synthesis of Hexahydrodiimidazodiazepines Heterocyclic Peptidomimetics and Their in Vitro and in Vivo Activities at μ (MOR), δ (DOR), and κ (KOR) Opioid Receptors," *J. Med. Chem.*, 2015; 58(12): 4905-4917.
Ferrell, B. et al., Collaborators, "Pharmacological management of persistent pain in older persons," American Geriatrics Society Panel on the Pharmacological Management of Persistent Pain in Older Persons, *Pain Med.*, 2009; 10:1062-1083.
Forbes, J. M. et al., "Mechanisms of Diabetic Complications," *Physiol. Rev.* 2013; 93:137-188.
George, J. et al., "Locally mediated analgesic effect of bradykinin type 2 receptor antagonist HOE 140 during acute inflammatory pain in rats," *J Burn Care Res.*, Nov.-Dec. 2014; 35(6) :e391-398.
Harris, R. E. et al., "Decreased central mu-opioid receptor availability in fibromyalgia," *J Neurosci.* 2007; 27(37): 10000-10006.
Jiang, Y.-L. et al., "Analgesic roles of peripheral intrinsic met-enkephalin and dynorphin A in long-lasting inflammatory pain induced by complete Freund's adjuvant in rats," *Exp Ther Med.*, 2015; 9: 2344-2348.
Kannampalli, P. et al., "Role of Principal Ionotropic and Metabotropic Receptors in Visceral Pain," *J. Neurogastroenterol. Motil.* 2015 21(2): 147-158.
Knezevic, N. N. et al., "Basic/Translational Development of Forthcoming Opioid- and Nonopioid-Targeted Pain Therapeutics," *Anesth. Analg.* 2017; 125:1714-1732.
Krebs, E. E. et al., "Effect of Opioid vs Nonopioid Medications on Pain-Related Function in Patients with Chronic Back Pain or Hip or Knee Osteoarthritis Pain: The SPACE Randomized Clinical Trial," *JAMA*, 2018; 319(9): 872-882.
Loeser, R. F. et al., "Osteoarthritis: A disease of the joint as an organ," *Arthritis Rheum.*, 2012; 64(6): 1697-1707.
Mangel, A. W. et al., "Clinical trial: asimadoline in the treatment of patients with irritable bowel syndrome," *Aliment. Pharmacol. Ther.*, 2008; 28(2): 239-249.
Mantyh, P., "Bone cancer pain: causes, consequences, and therapeutic opportunities," *Pain*, 2013; 154(S1): S54-62.

(Continued)

*Primary Examiner* — Sarah Pihonak
(74) *Attorney, Agent, or Firm* — Cooley LLP; J. Dean Farmer; Serge R. Banini

(57) ABSTRACT

The present disclosure teaches the use of a dual-acting opioid agonist for the treatment of pain (e.g., inflammatory pain). The opioid agonist activates both the kappa and delta opioid receptors to provide synergistic reduction in pain. The opioid agonist is peripherally restricted and does not cross the blood-brain barrier.

20 Claims, 10 Drawing Sheets

(56) References Cited

OTHER PUBLICATIONS

Mantyh, P., "Bone Cancer Pain: From Mechanism to Therapy." *Curr Opin Support Palliat Care*. 2014; 8(2): 83-90.
Mastrangelo, F. et al., "Low-Grade Chronic Inflammation Mediated by Mast Cells in Fibromylagia: Role of IL_37," *J. Biol. Regul. & Homeost. Ag*. 2018; 32(2): 195-198.
Merighi, S. et al., "Morphine mediates a proinflammatory phenotype via µ-opioid receptor-PKCε-Akt-ERK 1/2 signaling pathway in activated microglial cells," *Biochem Pharmacol*., 2013; 86(4): 487-96.
Mika, J. et al., "Delta-Opioid Receptor Analgesia Is Independent of Microglial Activation in a Rat Model of Neuropathic Pain" *PLOS One*, 2014; 9(8): e104420.
Murase, S. et al., "Bradykinin and nerve growth factor play pivotal roles in muscular mechanical hyperalgesia after exercise (delayed-onset muscle soreness)," *J Neurosci*, 2010; 30: 3752-3761.
Ostling, P. S. et al., "America's Opioid Epidemic: a Comprehensive Review and Look into the Rising Crisis," *Curr Pain Headache Rep*., 2018; 22(5): 32.
Petho, G. et al., "Sensory and Signaling Mechanisms of Bradykinin, Eicosanoids, Platelet-Activating Factor, and Nitric Oxide in Peripheral Nociceptors," 2012; *Physiol. Rev*. 92:1699-1775.
Reville, B. et al., "The global sate of palliative care-progress and challenges in cancer care," *Ann Palliat Med*., 2014; 3(3): 129-138.
Ribeiro, V. G. C. et al., "Inflammatory biomarkers responses after acute whole body vibration in fibromyalgia," *Braz J Med Biol Res*., Mar. 1, 2018; 51(4): e6775.
Riviere, P. J. M., "Peripheral kappa-opioid agonists for visceral pain," *Br J Pharmacol*., 2004; 141: 1331-1334.
Salemi, S. et al., "Up-regulation of delta-opioid receptors and kappa-opioid receptors in the skin of fibromyalgia patients," *Arthritis Rheum*., 2007; 56(7): 2464-2466.
Sengupta, J. N. et al., "Effects of kappa opioids in the inflamed rat colon," *Pain*, Feb. 1999; 79(2-3): 175-185.
Soelberg, C. D. et al., "The US Opioid Crisis: Current Federal and State Legal Issues," *Anesth & Analg*., 2017; 125(5): 1675-1681.
Sommer, C. et al., "Recent findings on how proinflammatory cytokines cause pain: peripheral mechanisms in inflammatory and neuropathic hyperalgesia," *Neurosci. Lett*., 2004; 361: 184-187.
Stein, C. et al., "Peripheral mechanisms of pain and analgesia," *Brain Res Rev*., 2009; 60: 90-113.
Totsch, S. K. et al., "Immune system involvement is specific pain syndromes," *Molecular Pain*, 2017; 13:1-17.
Wallace, M. S. et al., "A Phase II, multicenter, randomized, double-blind, placebo-controlled crossover study of CJC-1008-a long-acting, parenteral opioid analgesic—in the treatment of postherpetic neuralgia," *J Opioid Manag*., 2006; 2(3): 167-173.
Yamamoto, J. et al., "Down-regulation of mu opioid receptor expression within distinct subpopulations of dorsal root ganglion neurons in a murine model of bone cancer pain," *Neuroscience*, 2008; 151(3): 843-853.
Hartrick, C. T. et al., "Dual-Acting Peripherally Restricted Delta/Kappa Opioid (CAV1001) Produces Antinociception in Animal Models of Sub-Acute and Chronic Pain," Journal of Pain Research, 13:2461-2474 (2020).
Cowan, A., "Animal models of pain," Novel Aspects of Pain Management: Opioids and Beyond, Jana Sawynok and Alan Cowan, Ed., ISBN:0-471-180173, pp. 21-47 (1999).

+++ p<0.001; ++++ p<0.0001

+++ p<0.001; ++++ p<0.0001

++ $p<0.01$; * $p<0.05$; *** $p<0.001$

+++ p<0.0001

PERIPHERALLY-RESTRICTED DUAL-ACTING KAPPA AND DELTA OPIOID AGONIST FOR ANALGESIA IN PAIN STATES INVOLVING THE INFLAMMATORY RESPONSE

CROSS REFERENCE TO RELATED APPLICATIONS

This application is a U.S. National Phase Application, filed under 35 U.S.C. § 371, of PCT/US2018/038936, filed Jun. 22, 2018, which claims priority to, and benefit of, U.S. Provisional Patent Application No. 62/529,285 filed Jul. 6, 2017, the contents of which are hereby incorporated by reference in their entirety.

FIELD OF THE DISCLOSURE

The present disclosure teaches the use of a dual-acting opioid agonist for the treatment of pain (e.g., inflammatory pain). The opioid activates both the kappa and delta opioid receptors to provide synergistic reduction in pain: dual agonism.

BACKGROUND OF THE DISCLOSURE

Opioid analgesics can be useful analgesics for the treatment of pain. These drugs, such as heroin and morphine, are agonists at mu opioid receptors (MORs) in the central nervous system. However, because these drugs can cross the blood-brain barrier to the central nervous system, their use can cause unwanted side effects such as addiction. Moreover, because not all pain is mediated by MORs, these drugs may also be only partially effective for the treatment of certain types of pain. Accordingly, there is a need for safe and effective analgesics for the treatment of pain (e.g., chronic and/or inflammatory pain) that do not suffer from the side effects of traditional opioids such as morphine.

According to the National Institute on Drug Abuse, more than 115 people died every day in 2017 after overdosing on opioids. The total economic cost of opioid misuse in the United States is $78.5 billion per year. The opioid crisis has been caused and/or exacerbated by over-prescription of opioid pain-relievers for the treatment of pain (Soelberg et al., *Anesth & Analg.* 2017; 125(5): 1675-1681). Specifically, prescription opioids can be highly addictive and are widely misused. Indeed, all mu-activating opioids including heroin, morphine, and many other commonly prescribed opioids for pain are potentially addictive (Ostling et al., *Curr Pain Headache Rep.* 2018; 22(5):32).

Despite their widespread use, many prescription opioids are poorly effective for certain types of pain such as inflammatory and/or chronic pain. For example, pain due to bone cancer can be only partially responsive to prescription opioids such as morphine that target mu-opioid receptors (MOR). Without wishing to be bound by theory, this is likely because MOR can be down-regulated in bone cancer and thus targeting MOR can result in only a partial response (Yamamoto et al, *A. Neuroscience.* 2008; 151(3):843-53). Moreover, in bone cancer, multiple other non-opioid pain pathways are active, including involvement of inflammatory mediators of bradykinin, further limiting the effectiveness of treatments that only target MOR (Mantyh, P. Bone cancer pain: causes, consequences, and therapeutic opportunities. *Pain.* 2013; 154(S1) :S54-62).

Additionally, in neuropathic pain there is a shift away from mu-opioid dominated pathways to noradrenergic pathways (Bee et al. *Pain.* 2011; 152(1): 131-9). Likewise, in fibromyalgia there is a reduced central MOR availability (Harris et al. *J Neurosci.* 2007; 12; 27(37):10000-6). The reduced activity of MOR in these and other types of pain can thus reduce the effectiveness of drugs such as traditional opioids that only target MOR (e.g., morphine).

Moreover, in all chronic pain states, mu-opioid agonists can themselves induce microglial activation that can in turn induce hyperalgesia, a lowered pain threshold, and a primed microglial phenotype that persists even after opioid discontinuation. This can worsen rather than alleviate chronic pain even after opioid discontinuation (Merighi et al. *Biochem Pharmacal.* 2013; 86(4): 487-96). Thus, in some cases patients suffering from chronic pain may realize incomplete relief when using traditional opioids such as morphine, even despite increasing doses. This cycle of increasing dosage without adequate pain relief can result in dependence and addiction.

On the other hand, due to concerns over addiction and overdose, others who experience chronic pain may suffer undertreatment (Reville et al. *Ann Palliat Med.* 2014; 3(3): 129-38). For instance, in many parts of the developing world, access to opioids even for acute pain and/or cancer pain can be restricted due to concerns over addiction and overdose outlined above (Id). Even in the United States, some patients can suffer from an undertreatment of pain. For example, patients with cognitive impairment and the elderly can be especially susceptible to the central nervous system effects of traditional opioids such as morphine and in some cases are not prescribed enough to meet their pain management needs (American Geriatrics Panel on the Pharmacological Management of Persistent Pain in Older Persons. *Pain Med.* 2009; 10:1062-1083). Furthermore, alternative effective analgesics are not available (Id). This represents a significant unmet medical need and is a significant public health crisis that does not receive adequate attention (Id).

Despite the unmet need for safe and effective pain relievers, no such drug is currently available. Accordingly, there is a need for a safe and effective pain treatment that does not have the drawbacks associated with traditional opioid drugs.

BRIEF SUMMARY OF THE DISCLOSURE

One aspect of the present disclosure relates to a method of treating pain in a subject in need thereof, the method comprising administering to the subject a therapeutically effective amount of Compound 1:

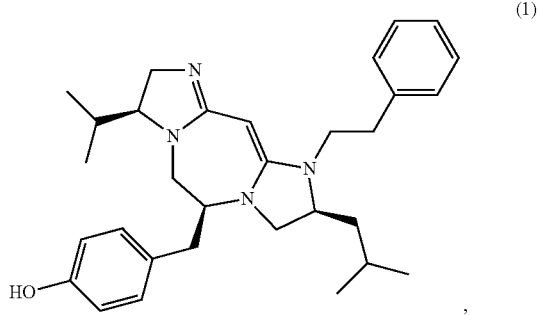 [SMILES: CC(C)C[C@H]1CN2C(=CC3=NC[C@H](C(C)C)N3C[C@@H]2Cc2ccc(O)cc2)N1CCc1ccccc1]

(1)

or a pharmaceutically acceptable salt, prodrug, solvate, hydrate, tautomer, or isomer thereof.

Another aspect of the present disclosure relates to the use of the Compound 1:

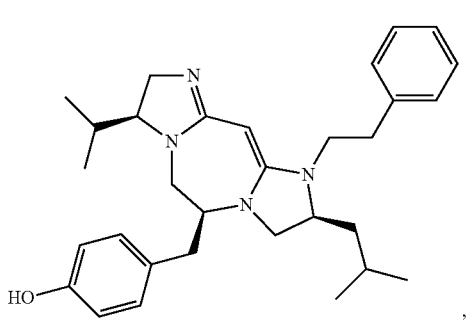

(1)

or a pharmaceutically acceptable salt, prodrug, solvate, hydrate, tautomer, or isomer thereof for the treatment of pain.

Another aspect of the present disclosure relates to the use of the Compound 1:

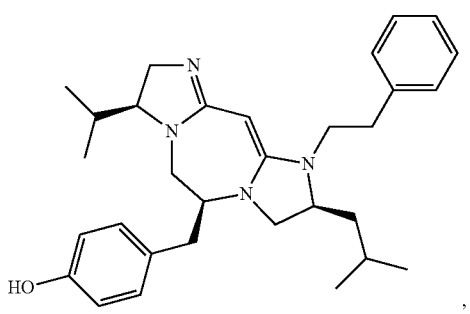

(1)

or a pharmaceutically acceptable salt, prodrug, solvate, hydrate, tautomer, or isomer thereof in the manufacture of a medicament for the treatment of pain.

One aspect of the present disclosure relates to a method of preventing pain in a subject in need thereof, the method comprising administering to the subject a therapeutically effective amount of Compound 1:

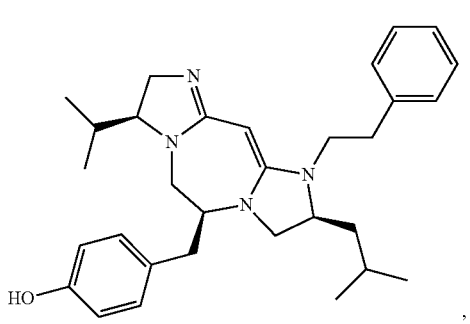

(1)

or a pharmaceutically acceptable salt, prodrug, solvate, hydrate, tautomer, or isomer thereof.

Another aspect of the present disclosure relates to the use of the Compound 1:

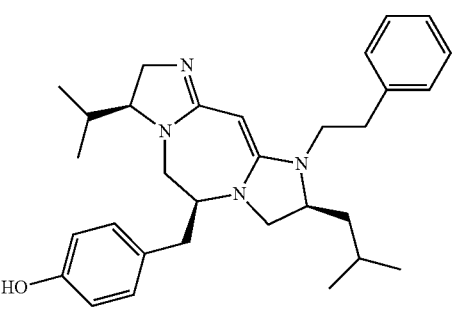

(1)

or a pharmaceutically acceptable salt, prodrug, solvate, hydrate, tautomer, or isomer thereof for the prevention of pain.

Another aspect of the present disclosure relates to the use of the Compound 1:

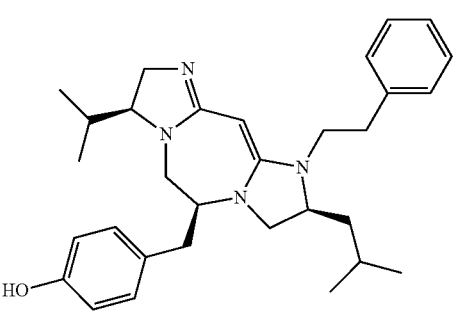

(1)

or a pharmaceutically acceptable salt, prodrug, solvate, hydrate, tautomer, or isomer thereof in the manufacture of a medicament for the prevention of pain.

Another aspect of the present disclosure relates to a pharmaceutical composition comprising Compound 1:

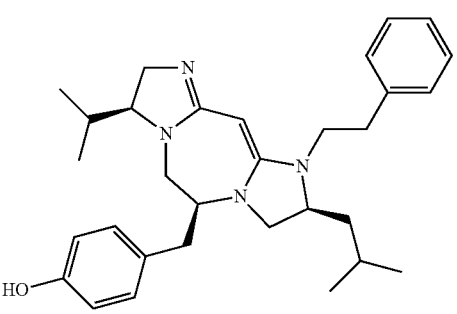

(1)

and a pharmaceutically acceptable carrier.

In one or more embodiments of any of the above aspects, the pain is caused by inflammation. In some embodiments, the pain is caused by the initiation of the inflammatory response. In some embodiments, the pain is associated with hyperalgesia.

In one or more embodiments, Compound 1 does not cross the blood-brain barrier. In one or more embodiments, Compound 1 does not affect the central nervous system. In one or more embodiments, Compound 1 activates kappa opioid receptors. In one or more embodiments, Compound 1 activates delta opioid receptors. In one or more embodiments, Compound 1 activates kappa and delta opioid receptors, in one or more embodiments, Compound 1 does not significantly activate mu receptors.

In one or more embodiments, the pain is chronic pain or subacute pain. In one or more embodiments, the chronic pain is arthritis pain, low back pain, neuropathic pain, visceral pain, pain due to cancer, pain due to injury, pain due to joint inflammation, pain due to back disorders, or neck pain. In one or more embodiments, the pain due to cancer is caused by cancer involving intraperitoneal abdominal and pelvic organs or bone cancer. In one or more embodiments, the pain due to injury is caused by bone, ligament, or tendon injury. In some embodiments, the pain is due to irritable bowel syndrome or interstitial cystitis. In some embodiments, the pain is due to inflammatory arthritis.

In one or more embodiments, Compound 1 reduces pain to a similar or greater degree as a central-nervous system-acting opioid. In one or more embodiments, the central-nervous system-acting opioid activates a mu receptor. In one or more embodiments, the central-nervous system-acting opioid is morphine.

In one or more embodiments, administrating Compound 1 does not result in any central-nervous system side effects. In one or more embodiments, the central nervous system side-effects are addiction, sedation, impaired mentation, somnolence, respiratory depression, nausea, constipation, dysphoria, or seizures. In one or more embodiments, administrating Compound 1 does not result in addiction.

In one or more embodiments, Compound 1 results in synergistic activation of kappa and delta opioid receptors. In one or more embodiments, the synergy results from the delta effect enhancing the kappa effect. In one or more embodiments, administration of Compound 1 is similar to or superior to a kappa receptor agonist for treatment of pain (e.g., inflammatory pain). In one or more embodiments, administration of Compound 1 is similar to or superior to a kappa receptor agonist for treatment of hyperalgesia. In one or more embodiments, administration of Compound 1 results in reduced urinary output compared to a kappa receptor agonist.

DETAILED DESCRIPTION OF THE DISCLOSURE

Figure 1:
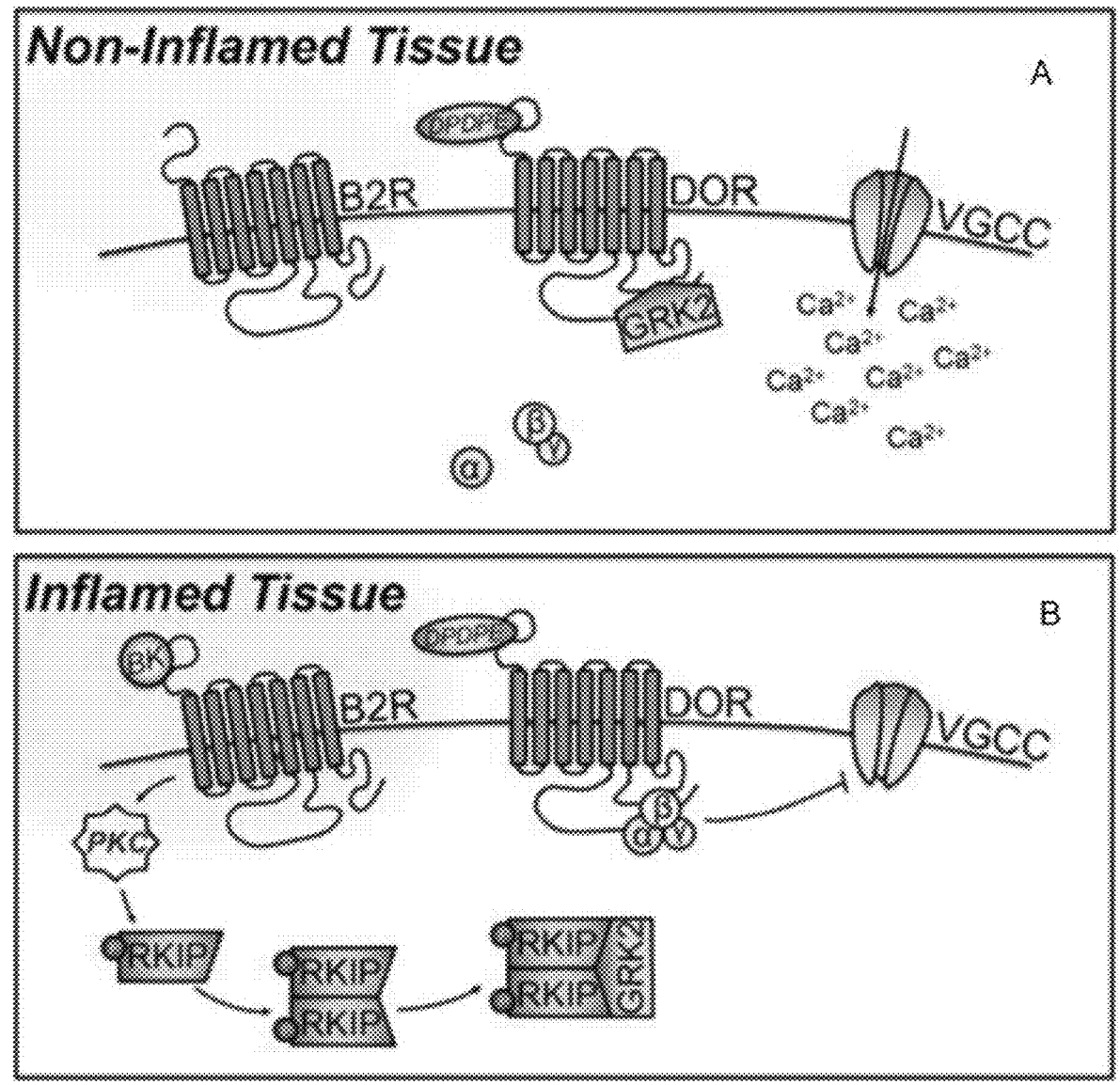
FIG. 1A is a graphic depicting the baseline biochemical state of uninflamed tissue.
FIG. 1B is a graphic depicting the biochemical response in tissue to inflammation.

Opioid analgesics are among the most important and powerful analgesics available. Many existing preparations rely on the mu opioid receptor in the central nervous system (i.e., brain and spinal cord) for their activity. Unfortunately, mu opioid agonism in the central nervous system can be responsible for some of the serious adverse effects associated with opioid analgesia including life-threatening respiratory depression and addiction. Further, mu opioid agonism can be responsible for other troublesome side effects including impaired mentation, somnolence, nausea and constipation.

In the peripheral tissues, mu receptors can be much less involved in the pain pathway. Different types of opioid receptors, namely the kappa and delta opioid receptors, can often be present in peripheral sensory nerves as well as the central nervous system. These too can be associated with other unwanted adverse effects, including dysphoria and seizures, due to their activity in the central nervous system.

The restriction of mu opioid agents to the peripheral nervous system (i.e., keeping opioid agents out of the central nervous system to avoid interaction with mu receptors there), can help avoid central adverse effects including the addictive potential and respiratory depression. However, because mu opioid receptors do not play a major role in the peripheral pain pathway, the effect of mu opioid agonism in the periphery can have minimal impact on analgesia.

Peripherally-restricted kappa opioid agonists (e.g., ICI204448) can sometimes provide relatively modest analgesia. The kappa receptor is, to a significant extent, under the influence of the normally quiescent delta opioid receptor through heterodimerization of the kappa and delta receptors. However, in the presence of inflammation, the delta receptor is unsequestered, allowing it to not only participate in analgesia itself, but also to boost the activity of the kappa receptor through allosteric modulation. Without wishing to be bound by theory, in the presence of inflammation, having both kappa and delta activity in the periphery can enhance the analgesic effect.

The present disclosure teaches a dual-acting, peripherally-restricted opioid with both kappa and delta effect, but minimal mu effect Compound 1, below). In some embodiments, Compound 1 has significantly improved analgesia compared to other analgesics such as pure kappa agonist agents (e.g., ICI204448) and/or pure mu agonist agents (e.g., morphine or heroin). In some embodiments, Compound 1 has increased analgesic effect in the presence of inflammation. In some embodiments, Compound 1 has limited potential for addiction (e.g., no potential for addiction). In some embodiments Compound 1 has limited potential for (e.g., no potential for) somnolence, respiratory depression, seizure, dysphoria, or constipation.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

"Inflammatory Response" (or inflammatory cascade) refers to the innate immune response to injury involving the elaboration of chemokines and inflammatory peptides such as bradykinin "VGCC" refers to voltage-gated calcium channel.

"B2R refers to bradykinin receptor B2, which is constitutively present in normal tissues.

"DPDPE" refers to (D-Pen2,D-Pen5)-Enkephalin, a selective delta opioid agonist.

"hyperalgesia" refers to an increased sensitivity to painful stimuli.

As used herein, "DOR" refers to delta opioid receptor. The term "KOR" refers to kappa opioid receptor, and "MOR" refers to mu opioid receptor.

As used herein, "GRK2" refers to G protein-coupled receptor kinase-2.

As used herein, "BK" refers to bradykinin.

As used herein, "PKC" refers to protein kinase C.

As used herein. "RKIP" refers to Raf kinase inhibitory protein.

As used herein, "CFA" refers to Complete Freund's Adjuvant.

As used herein, "JCT" refers to joint compression threshold.

As used herein, "SEM" refers to standard error of the mean

As used herein, "IP" refers to intraperitoneal administration.

As used herein, "PO" refers to "per os" or administration by mouth.

As used herein, "ANOVA" refers to analysis of variance.

As used herein, "IACUC" refers to the Institutional Animal Care and Use Committee.

As used herein, "SNL" refers to spinal nerve ligation.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

Subjects or patients "in need of treatment" with a compound of the present disclosure include patients with diseases and/or conditions that can be treated with the compounds of the present disclosure to achieve a beneficial therapeutic result. A beneficial outcome includes an objective response or a subjective response including self-reported reduction in pain. For example, a patient in need of treatment is suffering from pain and/or hyperalgesia. In some cases the patient is suffering from subacute (e.g., chronic) pain that can be caused by, for instance, arthritis or other inflammation.

As used herein, an "effective amount" (or "therapeutically effective amount") of a compound disclosed herein, is a quantity that results in a beneficial clinical outcome (e.g., pain reduction) of the condition being treated with the compound compared with the absence of treatment. The amount of the compound or compounds administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect.

The terms "treatment," "treat," and "treating," are meant to include the full spectrum of intervention in patients with "pain" with the intention to reduce, mollify or eliminate the pain from which the patient is suffering. Treating can be curing, improving, or at least partially ameliorating the patient's condition (e.g., pain).

"Prevention" or "Preemption" include reducing the expected or anticipated symptoms of a disease or condition before they are exhibited by a subject. For example, as set forth herein, pain (e.g., inflammatory pain) can be prevented or preempted in a subject at risk for pain (e.g., a subject with an inflammatory condition) by treatment with Compound 1. In some embodiments, treatment with Compound 1 in subjects who do not yet have pain can prevent the subject from experiencing pain. For example, as used herein, the onset of pain can be prevented by treating a subject with Compound 1 before the subject undergoes an event that may cause pain (e.g., an operation). For example, as used herein, a worsening of pain (e.g., more intense pain as self-reported by the subject) can be prevented by treating a subject with Compound 1 before the subject undergoes an event that may cause pain (e.g., an operation).

"Cancer" as defined herein refers to a new growth which has the ability to invade surrounding tissues, metastasize (spread to other organs) and which may eventually lead to the patient's death if untreated. "Cancer" can be a solid tumor or a liquid tumor.

Compound 1

As used herein, Compound 1 is understood as 4-(((2S,5S,8S)-2-isobutyl-8-isopropyl-1-phenethyl-2,3,5,6,8,9-hexahydro-1H-diimidazo[1,2-d:2',1'-g][1,4]diazepin-5-yl)methyl)phenol. Compound 1 is a peripherally restricted opioid with agonist activity against kappa and delta receptors and the structure of Compound 1 is given below:

ICI204448

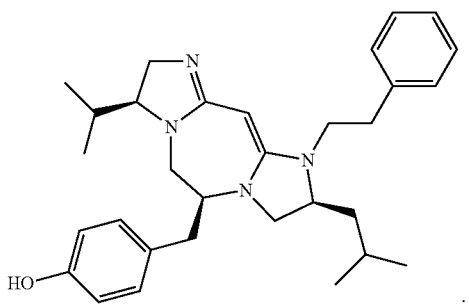

ICI204448 is a peripherally-restricted selective kappa opioid agonist. Its effects are evaluated in Example 1, below. It has the structure below:

Celecoxib

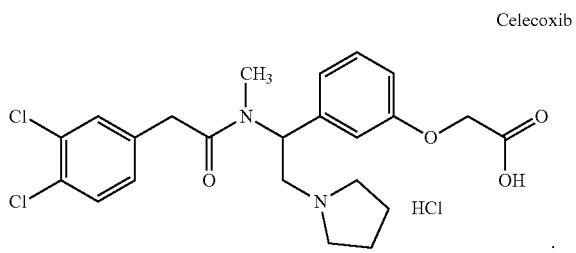 [SMILES: CN(C(=O)Cc1ccc(Cl)c(Cl)c1)C(CN1CCCC1)c1cccc(OCC(=O)O)c1 ; Cl]

Celecoxib is a COX-2 selective nonsteroidal anti-inflammatory drug of the formula:

Gabapentin

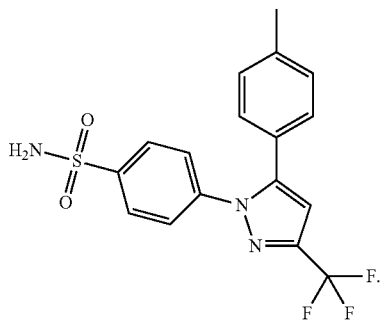

Gabapentin is a drug used to treat neuropathic pain. It has the structure:

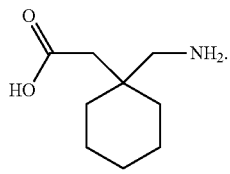

Proposed Mechanism of Action of Compound 1

FIG. 1 sets forth a proposed mechanism of action for Compound 1. Without wishing to be bound by theory, FIG. 1A shows a proposed native state for non-inflamed tissue. As shown in FIG. 1A, G protein-coupled receptor kinase-2 (GRK2) can bind to a delta opioid receptor (DOR), inactivating the DOR. Thus, the DOR does not affect the sensation of pain in the non-inflamed state.

FIG. 1B shows a proposed state of inflamed tissue. Without wishing to be bound by theory, in the inflamed state, proinflammatory bradykinin (BK) can stimulate GRK2 movement away from DOR and onto Raf kinase inhibitory protein (RKIP). This chain of events can allow the activation of the DOR. In particular, protein kinase C (PKC)-dependent RKIP phosphorylation associated with the binding of BK can induce GRK2 sequestration, restoring functionality of DOR in sensory neurons. Active DOR can then be available to participate in reducing the sensation of pain in subjects, e.g., in the inflamed state (Brackley et al., *Cell Rep.* 2016; 16(10):2 686-2698).

Furthermore, active DOR can allosterically enhance the activity of kappa opioid receptors (KOR), which are constitutively present in peripheral sensory neurons and are available to synergistically participate in reducing the sensation of pain in subjects (e.g., in the inflamed state). Accordingly, in some embodiments, GRK2 sequestration, e.g., upon inflammatory stimulus, can make DORs and KORs more efficient, providing the opportunity to reduce the sensation of pain in inflamed subjects.

For example, without wishing to be bound by theory, DORs and KORs can form heterodimers in peripheral sensory neurons (i.e., DOR-KOR heterodimers). Without wishing to be bound by theory, allosteric interactions in DOR-KOR heterodimers can modulate sensitivity to painful stimuli in the presence of inflammation. The activity of these heterodimers in animal models of pain has been demonstrated in peripheral sensory neurons (Berg et at, *Mol Pharmacol.* 2012; 81(2): 264-72). Allosteric interaction between the kappa and delta components is thought to contribute to the enhancement of kappa-mediated analgesia by delta agonists. Evidence for DOR-KOR heteromers in peripheral sensory neurons includes coimmunoprecipitation of DOR with KOR; that a DOR-KOR heteromer selective antibody augmented the antinociceptive effect of DPDPE (delta agonist) in vivo; and the DOR-KOR heteromer agonist 6-GNTI inhibited adenylyl cyclase activity in vitro as well as PGE2-stimulated thermal allodynia in vivo. Accordingly, without wishing to be bound by theory, DOR-KOR heteromers can exist in primary sensory neurons and KOR active agents can act as modulators of DOR agonist responses, for instance through allosteric interactions between the promoters of the DOR-KOR heteromer.

Without wishing to be bound by theory, because Compound 1 does not cross the blood-brain barrier (BBB), it is proposed that Compound 1 does not suffer from the same shortcomings as traditional opioids. Specifically, because Compound 1 does not cross the BBB, and therefore does not significantly interact with mu opioid receptors, Compound 1 is less prone to result in addiction and other CNS-associated side effects such as constipation, impaired mentation, somnolence, and the like. Thus, in some embodiments, Compound 1 does not suffer from the same drawbacks as traditional opioids. In some embodiments, Compound 1 does not result in central nervous system side effects such as addiction.

Additionally, without wishing to be bound by theory, Compound 1 is effective at treating pain, e.g., inflammatory and/or chronic pain. As set forth above, Compound 1 is an effective agonist at both the kappa and de/ta opioid receptors. This dual activity can result in high levels of pain relief for patients, without the deleterious central nervous system effects associated with traditional opioids. Accordingly, in some embodiments, Compound 1 is administered to patients with greater safety than traditional opioid analgesics.

Formalin Model of Pain in Rodents

Without wishing to be bound by theory, as set forth in Example 1, mice were treated with formalin in a standard model for pain assessment in mice. Without wishing to be bound by theory, the formalin test in mice evaluates pain in two phases. Phase 1 can last for about 5-10 minutes after injection into the hind paws of mice. Phase 1 can evaluate the mice's response to the acute pain immediately following formalin (an irritating substance) injection. Accordingly, in some embodiments phase 1 of the formalin model can evaluate pain caused by the stimulation of nociceptors (i.e., phase 1 can evaluate nociceptive or acute pain).

Without wishing to be bound by theory, phase 2 of the formalin model can begin about twenty minutes after the initial injection of formalin. Phase 2 can represent and evaluate hyperalgesia initiated by the inflammatory process. For example, the inflammatory response can be triggered by tissue damage with subsequent sensitization of nociceptors. This sensitization process can take about twenty minutes to develop and can then be sustained for about 60 minutes or longer after injection. Accordingly, phase 2 measures inflammatory pain and the response thereto.

As set forth in Example 1 below, mice were tested in a formalin model for pain and were subsequently treated with (i) inert vehicle; (ii) low dose of a peripherally-restricted kappa opioid agonist (i.e., ICI204448); (iii) high dose of a peripherally-restricted kappa opioid agonist (i.e., ICI204448); (iv) low dose of Compound 1; and (v) high dose of Compound 1. Compared with inert vehicle and ICI204448, Compound 1 reduced pain in mice treated with formalin at about 20-25 minutes, 25-30 minutes, and 30-35 minutes (i.e., during phase 2).

As set forth in Example 1 and as shown in FIG. 2, only a small dose of Compound 1 was needed to produce the same effect as a high dose of the peripherally-restricted kappa opioid receptor agonist ICI204448) in phase 2 of the formalin model. Moreover, the high dose of Compound 1 was shown to produce complete elimination of the phase 2 hyperalgesic pain response in mice.

Figure 2A:
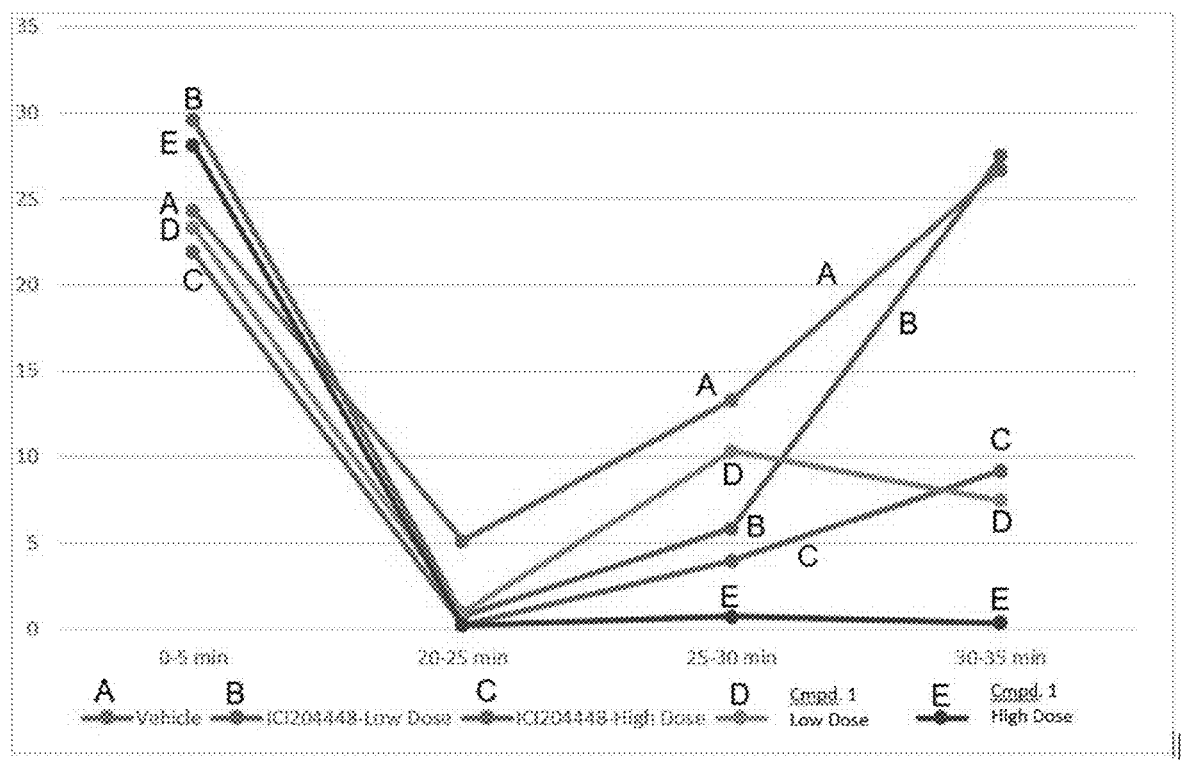
FIG. 2A is a line graph of the pain behaviors exhibited by the mice that received each dose of vehicle or drug as set forth in Example 1.
Figure 2B:
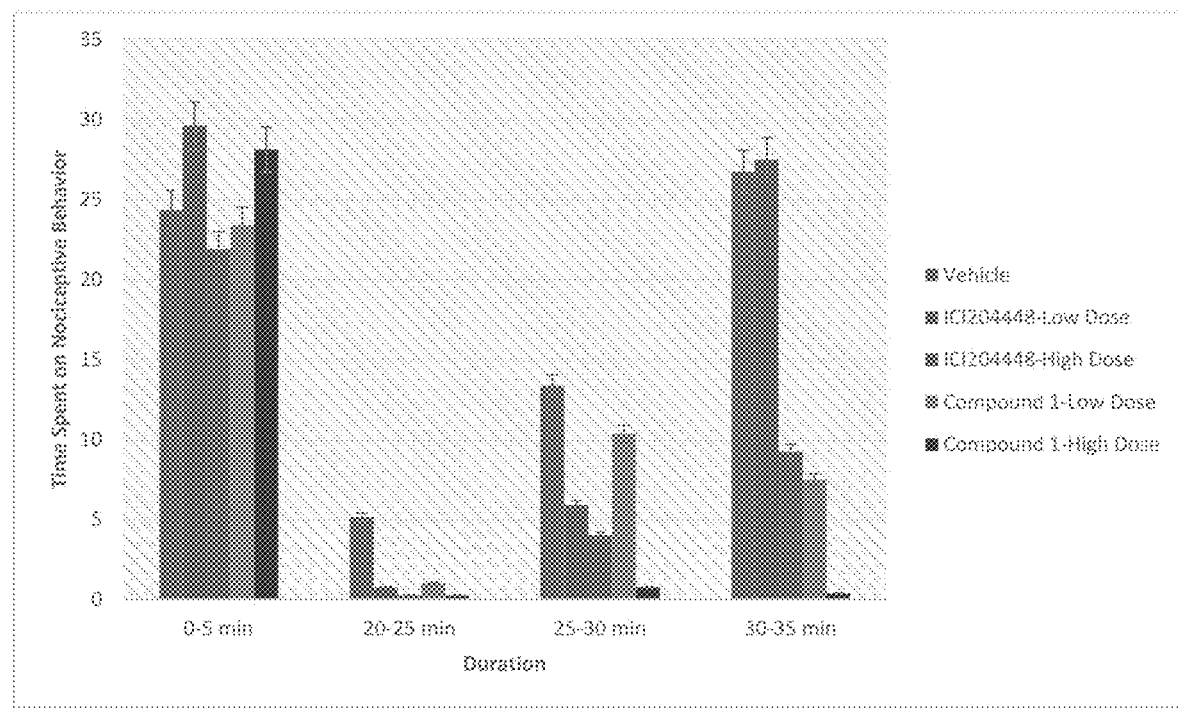
FIG. 2B is a bar graph of the pain behaviors exhibited by mice that received each dose of vehicle or drug as set forth in Example 1.

Accordingly, in some embodiments, the present disclosure teaches the treatment of pain (e.g., pain caused by inflammation or the initiation of the inflammatory response) by administering to a subject in need thereof an effective amount of Compound 1. In some embodiments, the magnitude of the reduction in pain is substantially similar to the reduction in pain caused by a central-nervous system-acting opioid (e.g., morphine). In some embodiments, Compound 1 is effective at reducing hyperalgesia (e.g., more effective than a kappa opioid receptor alone). In some embodiments, Compound 1 can simultaneously activate kappa and delta opioid receptors to result in a synergistic reduction in pain at lower doses than is observed with other drugs such as pure kappa agonists (e.g., ICI204448). For instance, it was found that Compound 1 was at least as effective as ICI204448 in reducing time spent on pain (i.e., nociceptive) behaviors at 30-35 minutes even though Compound 1 was administered at a dose of less than 10% of the amount of ICI204448 on a molar basis (FIGS. 2A and 2B).

Figure 3:
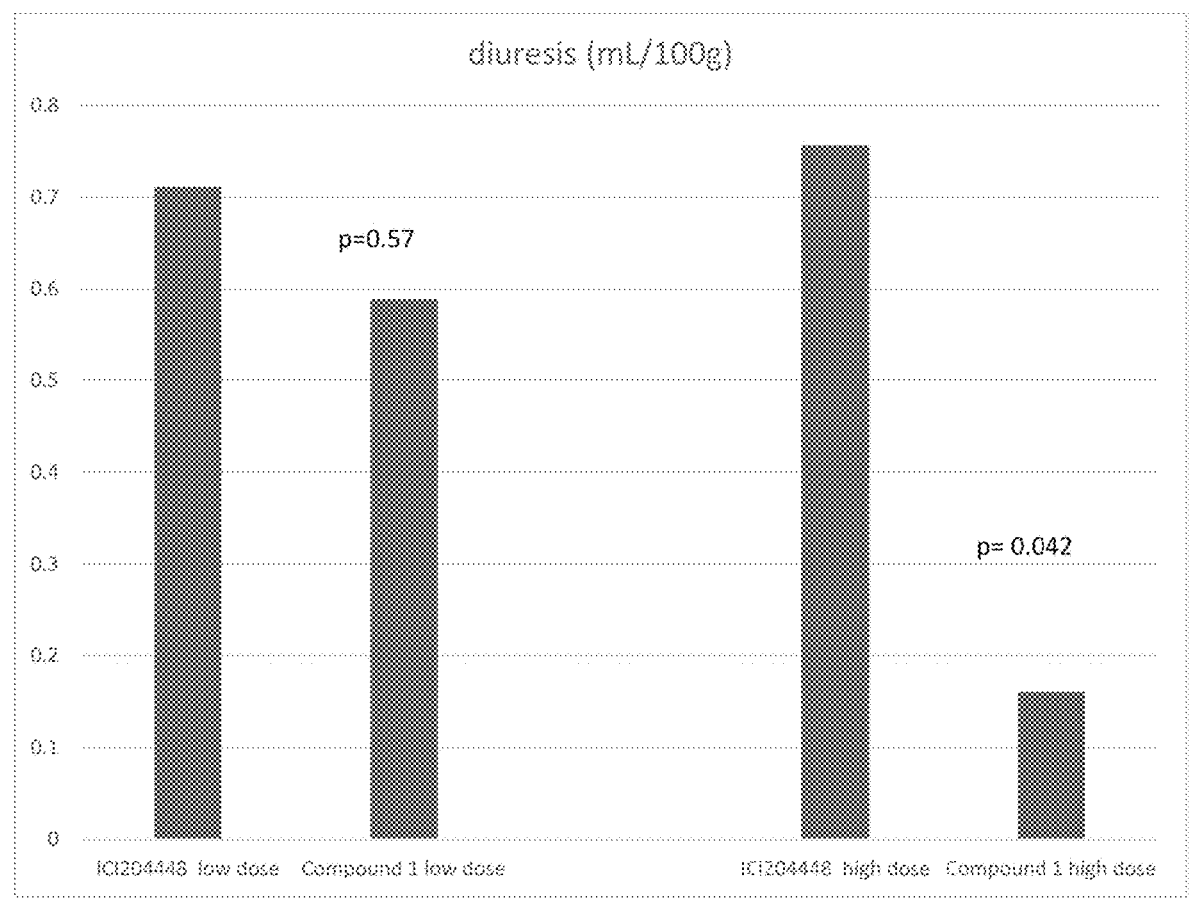
FIG. 3 is a bar graph depicting the urine output of mice that received each dose of Compound 1 or ICI204448 as set forth in Example 1.

As set forth in Example 1 and FIG. 3, mice that were treated with Compound 1 were found to produce less urine than mice treated with the kappa agonist ICI204448 over a 6-hour collection period following formalin testing. Accordingly, in some embodiments, treatment with Compound 1 can be less likely to result in diuresis compared with other peripherally-restricted kappa opioid agonists (e.g., ICI204448).

Furthermore, as set forth in Example 1, animals were treated with Compound 1 before formalin injection. As shown in FIGS. 2A and 2B, animals that were treated with a high dose of Compound 1 did not exhibit any substantial pain behaviors at 20-25 min, 25-30 min, or 30-35 min. Accordingly, Example 1 suggests that Compound 1 can be administered before an injury (e.g., an injury that is likely to cause inflammation) and prevent the sensation of pain (e.g., pain due to inflammation). Accordingly, in some embodiments Compound 1 can be used to prevent pain (e.g., pain due to inflammation).

Arthritis Model of Pain in Rats

Example 2 below evaluated the efficacy of a single intraperitoneal (IP) injection of Compound 1 in a model of rheumatoid arthritis in rats. As demonstrated in Example 2, a single intraperitoneal dose of Compound 1 significantly reduced established mechanical hyperalgesia due to CFA-induced rheumatoid arthritis in the rat in a time- and dose-dependent manner.

Without wishing to be bound by theory, as set forth in Example 2, rats were administered Compete Freund's Adjuvant (CFA) to produce an arthritis-like response. After two weeks, and once an inflammatory response had developed, rats were treated with inert vehicle, Compound 1, or celecoxib (a cyclo-oxygenase-2 (COX-2) anti-inflammatory drug). Joint compression thresholds (JCTs) were measured before and after treatment with vehicle, Compound 1 or celecoxib as a proxy for pain thresholds.

Figure 4:
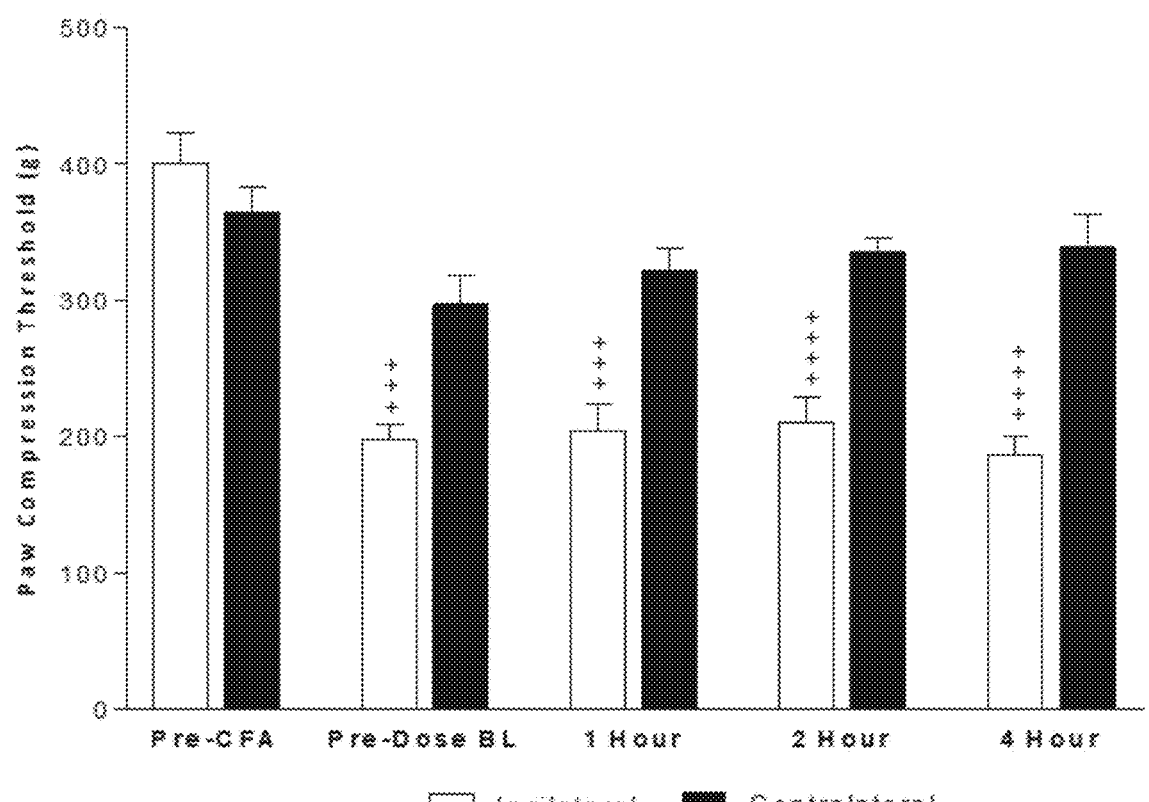
FIG. 4 is a bar graph comparing the joint compression thresholds between the ipsilateral and contralateral legs of injured rats at various time points in Example 2.

FIG. 4 shows the contrast between the JCTs for the injured (i.e., ipsilateral) vs, non-injured (i.e., contralateral) legs for rats administered vehicle. FIG. 4 demonstrates that for rats that did not receive either Compound 1 or celecoxib, the JCT for the injured leg was about two-thirds that of the JCT for the non-injured leg, suggesting that the injured leg was more painful than the non-injured leg.

Figure 5:
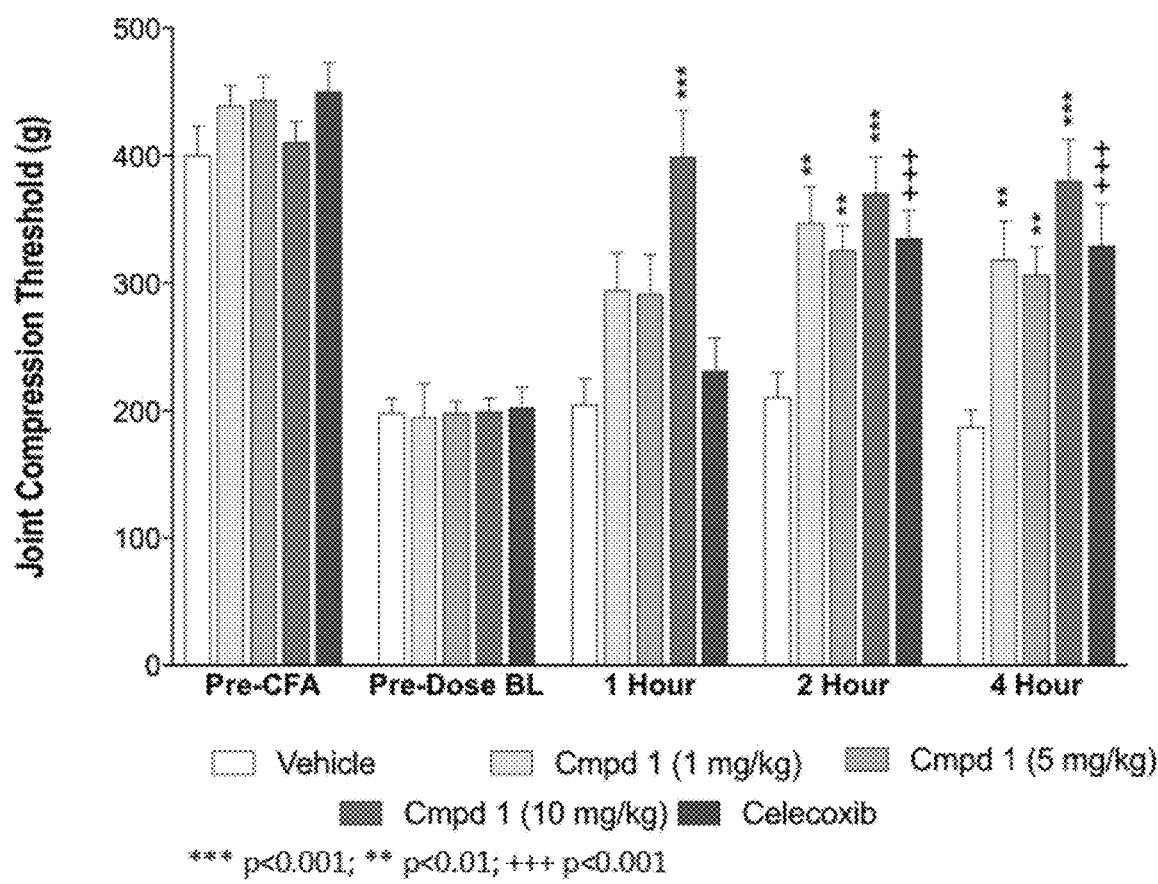
FIG. 5 is a bar graph showing the effects of Compound 1 on CFA-induced mechanical hyperalgesia in Example 2.

FIG. 5 compares the JCTs at one, two and four hours after administration of vehicle, Compound 1, or celecoxib. As shown in FIG. 5, all three doses of Compound 1 (i.e., 1, 5 and 10 mg/kg) led to significant increases in JCT, suggesting a decrease in pain sensation in rats. The results demonstrate that Compound 1 was able to reverse mechanical hyperalgesia in the injured leg after administration.

Accordingly, Example 2 is an exemplary model of a chronic pain state with a predominant inflammatory component. The combination of peripherally restricted delta and peripherally restricted kappa agonism from Compound 1 resulted in an attenuation of pain behaviors that was greater than that seen with an anti-inflammatory drug. Specifically, the response in the rheumatoid arthritis model was comparable or superior to celecoxib.

Neuropathic Pain Model in Rats

Example 3 below evaluated the efficacy of a single intraperitoneal injection of Compound 1 and the comparator, gabapentin, in the spinal nerve ligation (SNL) model for neuropathic pain in the rat. As demonstrated in Example 3, intraperitoneal injection of Compound 1 produced a time- and dose-dependent analgesic effect on mechanical hyperalgesia associated with SNL-induced neuropathic pain in the rat.

Without wishing to be bound by theory, as set forth in Example 3, rats were subject to spinal nerve ligation to produce a neuropathic-type response. After fifteen days, once a neuropathic response had developed, rats were treated with inert vehicle, Compound 1, or gabapentin. Paw compression thresholds were measured before and after treatment with vehicle, Compound 1 or gabapentin as a proxy for pain thresholds. Paw compression thresholds were measured using the same technique and device as the joint compression thresholds outlined above in the arthritis pain model, but were evaluated on the paw instead of on the ankle.

Figure 6:
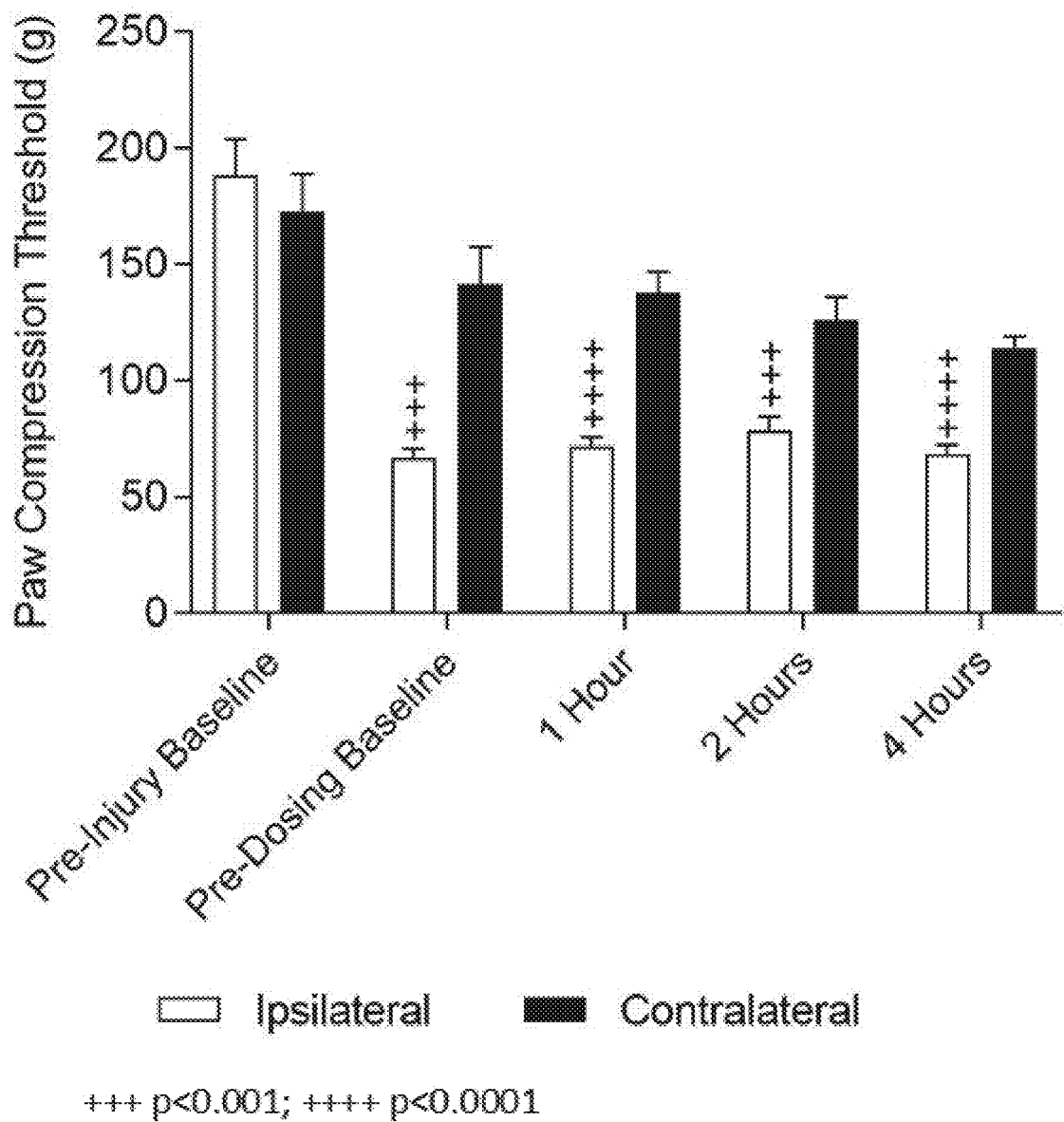
FIG. 6 is a bar graph comparing the paw compression thresholds between the ipsilateral and contralateral legs of injured rats at various time points in Example 3.

FIG. 6 shows the contrast between paw compression thresholds for the injured (i.e., ipsilateral) vs. non-injured (i.e., contralateral) legs for rats administered vehicle. FIG. 4 demonstrates that for rats that did not receive either Compound 1 or gabapentin, the paw compression thresholds for the injured leg was about one half that of the paw compression threshold of the non-injured leg, suggesting that the injured leg is more painful than the non-injured leg.

Figure 7:
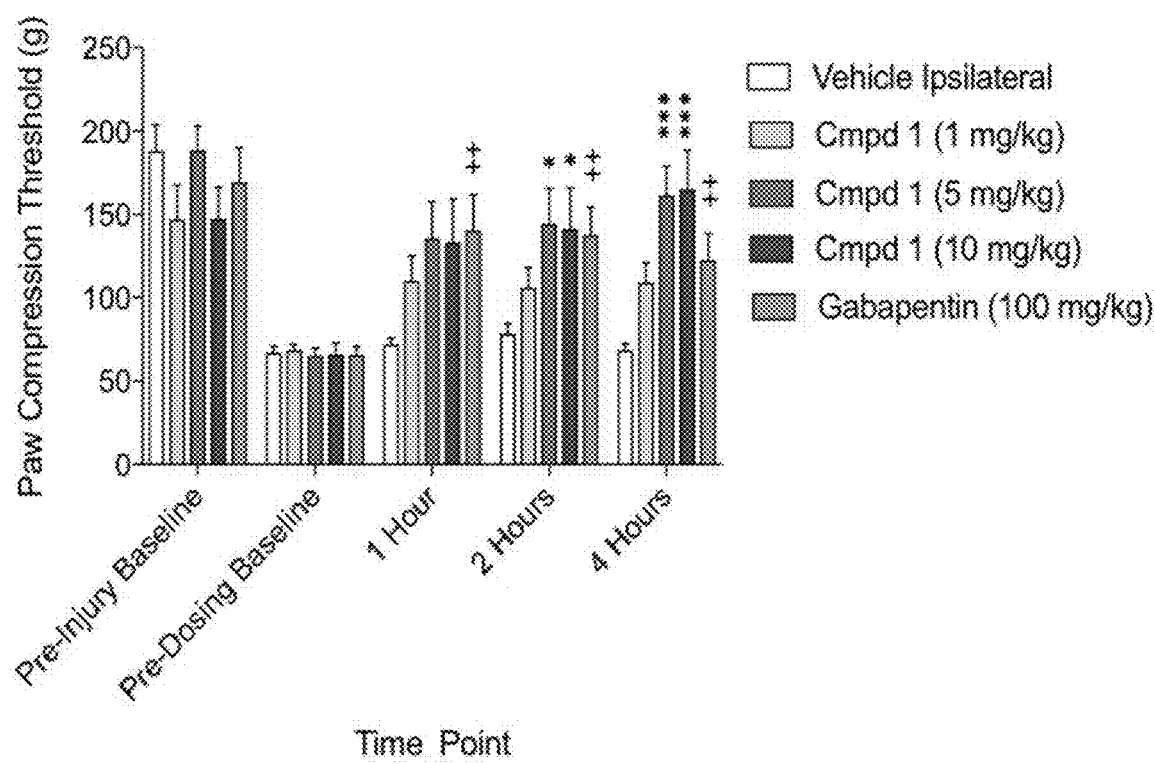
FIG. 7 is a bar graph showing the effect of Compound 1 on SNL-induced mechanical hyperalgesia in Example 3.

FIG. 7 compares the paw compression thresholds at one, two, and four hours after administration of vehicle, Compound 1, or gabapentin. As shown in FIG. 7, the 5- and 10-mg doses of Compound 1 led to significant increases in paw compression thresholds at the 2- and 4-hour time points, suggesting a decrease in pain sensation in the injured leg.

Accordingly, Example 3 suggests that in chronic neuropathic pain states, characterized by relative mu-opioid resistance and significant inflammatory response, moderate doses of Compound 1 are as effective or superior to gabapentin. Thus, in some embodiments the present disclosure provides for the treatment of neuropathic (e.g., chronic neuropathic) pain comprising administering Compound 1.

Bone Cancer Model of Pain in Rats

Without wishing to be bound by theory, Example 4 below evaluated the efficacy of a single intraperitoneal injection of Compound 1, and the comparator, subcutaneous morphine, in the MRMT-1 model of osteolytic cancer pain in rats. As shown in Example 4, Compound 1 administered at 10 mg/kg (IP) had a significant effect on osteolytic bone cancer pain induced by MRMT-1 inoculation with a slower onset compared to morphine.

As set forth in Example 4, rats were injected with MRMT-1 cancer cells to induce bone cancer in one of the hind legs. After 21 days, after the development of bone cancer, the rats were evaluated to measure the percent of weight bearing of each hind leg (i.e., injured vs. non-injured) as a proxy for pain in each leg.

Figure 8:
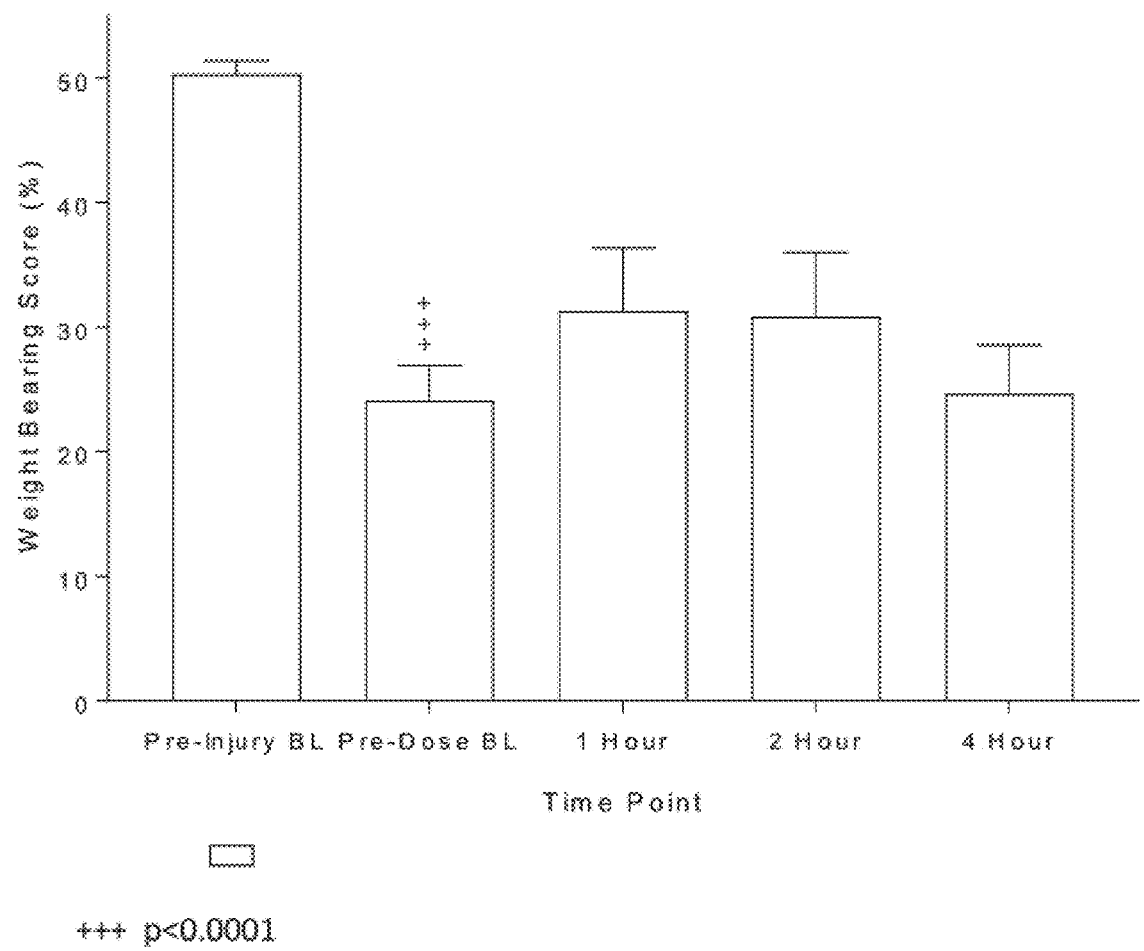
FIG. 8 is a bar graph depicting the percent of weight bearing of the injured leg for untreated rats after the development of bone cancer at various time points in Example 4.

FIG. 8 shows the percent weight bearing scores for rats that were administered vehicle at time points pre-injury, pre-injection with vehicle, and at 1, 2 and 4 hours after injection with vehicle. FIG. 8 shows that there was substantial variability between the pre-dose baseline measurement and the 1- and 2-hour time points, partially due to the fact that not all rats exhibited symptoms bone cancer. As a result of this variability, and in the interest of obtaining a reliable data set, the originally-proposed grouping of five groups with ten rats each was reconsidered in favor of three groups with thirteen rats each. The three evaluated groups were: Group 1 (treated with vehicle); Group 4 (treated with 10 mg/kg Compound 1); and Group 5 (treated with 6 mg/kg morphine). Groups 2 and 3, which had originally been proposed to evaluate the effects of Compound 1 at 1 and 5 mg/kg respectively, were not evaluated.

Figure 9:
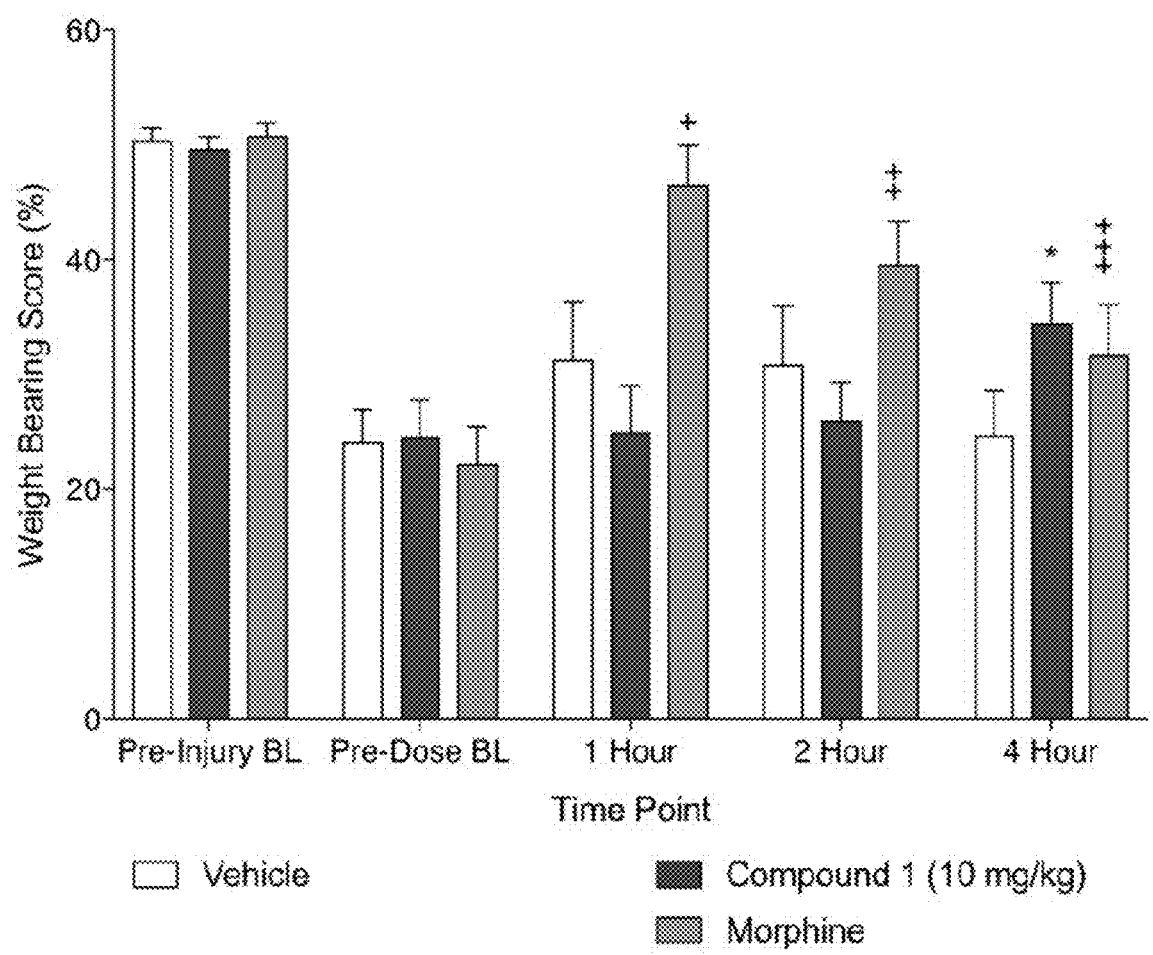
FIG. 9 is a bar graph showing the effect of Compound 1 on bone cancer pain as measured by the percent of weight bearing by the injured leg.

FIG. 9 shows the percent weight bearing score for rats at one, two and four hours after administration with vehicle, Compound 1, or morphine. As shown in FIG. 9, Compound 1 had a significant effect on osteolytic bone cancer pain induced by MRMT-1 cancer cells with a slower onset compared to morphine.

Bone cancer pain, despite relative resistance to opioids, typically only responds to strong mu-opioid treatment. The degree of inflammation, while present, is not as pronounced as in the previously referenced chronic pain conditions. Compound 1 produced a delayed reduction in pain behaviors associated with bone cancer pain in a single dose study. Without wishing to be bound by theory, chronic dosing could be useful to address chronic pain (e.g., pain due to cancer such as bone cancer).

Pain Indications

Thus, in some embodiments, Compound 1 can be used in the treatment of pain. The pain can be inflammatory pain, or pain caused by the initiation of the inflammatory response in a subject. In some embodiments, the pain can be due to an autoimmune disorder or other inflammatory disorder. In some embodiments, the pain can be due to arthritis. For example, the pain can be due to rheumatoid arthritis, osteoarthritis (e.g., osteoarthritis with synovitis) posttraumatic arthritis, or inflammatory arthritis.

In some embodiments, the pain is due to inflammatory bowel disease, irritable bowel syndrome, peritonitis, pleuritic pain, pelvic inflammation, fibromyalgia, or interstitial cystitis.

In some embodiments, the pain is neuropathic pain. For example, the pain can be due to complex regional pain syndrome, radiculitis, or inflammatory neuritis. In some embodiments, the pain is due to neuralgia (e.g., postherpetic neuralgia).

In some embodiments, the pain can be due to cancer. The cancer can be primary cancer or metastatic cancer. In some embodiments, the pain is due to cancer involving the thoracic organs, intraperitoneal organs, abdominal organs, pelvic organs, or bone cancer. Pain can be due to carcinomatosis. Pain can be due to an infectious process of the intrapleural space and/or intrapleural inflammation (e.g., pleurisy). Pain can be due to intraperitoneal inflammatory processes. For example, pain can be due to intraperitoneal inflammatory processes involving the pancreas (e.g., pancreatitis), liver, bowel, spleen, or urinary bladder (e.g., pelvic inflammatory disease and/or interstitial cystitis).

In some embodiments, the pain can be due to injury (e.g., tissue injury). In some embodiments, the pain is due to joint injury, bursa injury, muscle injury, bone injury, ligament injury, or tendon injury.

In some embodiments, the pain is arthritis pain, low back pain (e.g., pain due to back disorders), neuropathic pain, visceral pain, or neck pain. In some embodiments, the back (e.g., low back) and/or neck pain can be with or without radiculopathy. Pain can be due to musculoskeletal injury, tendonitis, and/or myofascial pain syndrome. The pain can be chronic pain or subacute pain.

In some embodiments, the pain is due to chronic inflammatory pain states (e.g., chronic inflammatory pain states with hyperalgesia). In some embodiments, the pain is due to acute and/or subacute pain states (e.g., acute and/or subacute pain states with hyperalgesia). For example, in some embodiments, the pain can be due to postoperative and/or posttraumatic pain (e.g., burn pain).

Pharmaceutical Compositions and Methods of Treatment

The present disclosure is also directed to methods of treatment involving the administration of Compound 1 of the present disclosure, or a pharmaceutical composition comprising Compound 1. The pharmaceutical composition or preparation described herein may be used in accordance with the present disclosure, e.g., for the treatment of pain (e.g., inflammatory pain) or hyperalgesia.

Compound 1, utilized in the treatment methods of the present disclosure, as well as the pharmaceutical compositions comprising it, may accordingly be administered alone, or as part of a treatment protocol or regiment that includes the administration or use of other beneficial compounds (e.g., as part of a combination therapy).

In using the pharmaceutical compositions of Compound 1 described herein, pharmaceutically acceptable carriers can be either solid or liquid. Solid forms include powders, tablets, dispersible granules, capsules, cachets and suppositories. The powders and tablets can comprise from about 5 to about 95 percent active ingredient (i.e., Compound 1). Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., which is hereby incorporated by reference in its entirety.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection. Aerosol preparations suitable for inhalation may also be used. These preparations may include solutions and solids in powder form, which may be in combination with a pharmaceutically acceptable carrier, such as an inert compressed gas, e.g., nitrogen. Also contemplated for use are solid form preparations that are intended to be converted, shortly before use, to liquid form preparations for either oral or parenteral administration. Such liquid forms include solutions, suspensions and emulsions.

Dosage

The amount and frequency of administration of Compound 1 and/or the pharmaceutically acceptable salts thereof will be regulated according to the judgment of the attending clinician considering such factors as age, condition and size of the patient as well as severity of the symptoms being treated. Effective dosage amounts of Compound 1, when used for the indicated effects, range from about 0.5 mg to about 5000 mg of Compound 1 as needed to treat the condition. Compositions for in vivo or in vitro use can contain about 0.5, 5, 20, 50, 75, 100, 150, 250, 500, 750, 1000, 1250, 2500, 3500, or 5000 mg of Compound 1, or, in a range of from one amount to another amount in the list of doses. A typical recommended daily dosage regimen for oral administration can range from about 1 mg/day to about 500 mg/day or 1 mg/day to 200 mg/day, in a single dose, or in two to four divided doses. In one embodiment, the daily dose regimen is 150 mg.

In some embodiments, Compound 1 can be administered for one day, two days, three days, four days, five days, six days, or seven days. In some embodiments, Compound 1 can be administered one week, two weeks, three weeks, or four weeks. In some embodiments, Compound 1 can be administered one month, two months, three months, four months, five months, six months, or longer. In some embodiments, Compound 1 can be administered indefinitely (e.g., chronic dosing).

Compound 1, with or without an additional therapeutic agent, can be administered by any suitable route. The compound can be administered orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986, which is hereby incorporated by reference in its entirety). Compound 1 can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers can be biocompatible, i.e., non-toxic, non-inflammatory, non-immunogenic and devoid of other undesired reactions at the administration site. Additionally, Compound 1 can be administered parenterally, subcutaneously, intramuscularly or intravenously. Compound 1 can be administered intraperitoneally.

Illustrative pharmaceutical compositions are tablets and gelatin capsules comprising Compound 1 and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

If formulated as a fixed dose, such pharmaceutical compositions employ Compound 1 within the dosage range described herein, or as known to those skilled in the art.

Since Compound 1 is intended for use in pharmaceutical compositions a skilled artisan will understand that it can be provided in substantially pure form for example, at least 60% pure, at leak 75% pure, at least 85% pure, at least 98% pure and at least 99% pure (w/w). The pharmaceutical preparation may be in a unit dosage form. In such form, the preparation is subdivided into suitably sized unit doses containing appropriate quantities of Compound 1, e.g., an effective amount to achieve the desired purpose as described herein (e.g., pain reduction).

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Formalin Model of Pain in Mice

The objective of this study was to evaluate the effects of Compound 1 and a peripherally-restricted kappa agonist (ICI204448) on formalin-evoked spontaneous nociceptive behaviors in mice. The study was performed by video recording of formalin-induced nociceptive behavior and then off-line scoring using a computer.

Subcutaneous plantar injection of formalin causes a bi-phasic nocifensive behavioral response in rodents. The early phase (phase 1) lasts for about 5-10 minutes, following which an interphase occurs without any discernible nociceptive reactions, after which the late phase (phase 2) nociceptive reaction ensues continuing from about 20-60 min following formalin injection. Thus, phase 2 of the formalin model is a model of continuously present, persistent pain, and is widely used for rapid screening of novel analgesic compounds. The model encompasses inflammatory, neurogenic and central mechanisms of nociception, and the late phase (phase 2), in particular, is considered as a pharmacodynamic surrogate of central sensitization.

In the present study, the effects of Compound 1 and ICI204448 were assessed from 0-5 minutes for the early phase (phase 1) and from 20-35 minutes for the late phase (phase 2) of formalin-induced nociceptive behavior.

Methods

Following IACUC approval and acclimation C57BL6 mice (Charles River Canada Inc.), 20-30 g, were randomly assigned into groups with 8 mice per group as provided in Table 1:

TABLE 1

| Study Design | | | | | | |
|---|---|---|---|---|---|---|
| Groups | Group treatment | Dose level (mg/kg) | Route | Dose volume (mL/kg) | Pre-treatment time | N |
| 1 | Vehicle (1:1:8 ethanol: Tween 80: 0.9% saline) | 0 | IP | 20 | 30 min | 8 |
| 2 | ICI204448—Low Dose | 1 | IP | 20 | 30 min | 8 |
| 3 | ICI204448—High Dose | 10 | IP | 20 | 30 min | 8 |
| 4 | Compound 1—Low Dose | 1 | IP | 20 | 30 min | 8 |
| 5 | Compound 1—High Dose | 10 | IP | 20 | 30 min | 8 |

All animals were acclimated to the observation chamber for about 15 minutes immediately prior to formal in injection. All animals received a 30 µL injection of freshly prepared formalin solution (5% in phosphate buffered saline; PBS) intra-plantarly (i.pl.) into the left hind paw. Animals were administered the vehicle, ICI204448 or Compound 1 intraperitoneally (IP) 30 minutes before formalin injection as depicted in the Table 1 above.

Following injection of the formalin all animals were returned immediately to the observation chamber and formalin-evoked spontaneous nociceptive behaviors in the mice were continuously recorded for 0-40 minutes using a commercial camcorder. The camera was turned on at least 5 minutes before formalin injection and verified for proper functioning.

Scoring from the recorded video files were done off-line using a computer by a blinded observer who has been validated to score such nociceptive behaviors in rodents. The total (cumulative) time spent in a 5-minute bin was recorded using a stop-watch for the following nociceptive behaviors: biting and licking of the formalin-injected paw.

Effects of the ICI204448 or Compound 1 were assessed in the following time periods: 0-5 minutes for the early phase (phase 1) and 20-35 minutes for the late phase (phase 2).

Mice were injected with formalin in the hind paw after pretreatment with vehicle, high and low doses of a peripherally-restricted kappa opioid agonist (ICI204448) and high and low doses of the peripherally-restricted Compound 1. Pain was measured for 35 minutes after injection. Additionally, urine output was measured using metabolic cages in each group of mice. Total urine volumes were collected over six hours.

Results

FIGS. 2A and 2B show a line graph and a bar graph, respectively, of the pain behaviors exhibited by the mice that received each dose of vehicle or drug. As shown in FIGS. 2A and 2B, compared with inert vehicle and ICI204448, Compound 1 reduced pain behaviors in mice treated with formalin at about 20-25 minutes, 25-30 minutes, and 30-35 minutes (i.e., phase 2). Additionally, only a small dose of Compound 1 (1 mg/kg) was needed to produce the same effect as a high dose of ICI204448. Moreover, the high dose of Compound 1 (10 mg/kg) was shown to produce complete elimination of the pain response in mice. A comparison of p values as a function of dose is given below in Table 2.

TABLE 2

Comparison of p Values by Dose

| Comparison | Timeframe | p Value |
|---|---|---|
| Compound 1 (high dose) v. vehicle | 30-35 min | p < 0.03 |
| Compound 1 (high dose) v. vehicle | 20-35 min | p < 0.003 |
| Compound 1 (high dose) v. KOR agonist (high dose) | 20-35 min | p < 0.01 |
| KOR agonist (high dose) v. vehicle | 20-35 min | p < 0.05 |

FIG. 3 shows a bar graph depicting the urine output of mice comparing ICI204448 to Compound 1. The resultant diuresis shown in FIG. 3 in mL urine collected over six hours has been normalized for mouse weight (mL per 100 g body weight). The p value comparing Compound. 1 high dose with low dose ICI204448 was p=0.57. The p value comparing Compound 1 high dose with high dose ICI204448 was p=0.042. The trend of Compound 1 was not suggestive of a diuretic effect. The normalized wine volumes collected for the kappa agonist were found to be consistent with prior studies investigating the overall kappa effect (See e.g., Barber et al., *Br. J. Pharmacol.*, (1994) 111, 843-851).

Example 2

Arthritis Model of Pain in Rats

This study evaluated the efficacy of a single intraperitoneal injection of Compound 1 on hyperalgesic nociceptive behaviors in an CFA (Complete Freund's Adjuvant) Model of Rheumatoid Arthritis Pain in Rats.

Rats have been used as a reliable animal model for the study of pain due to many similarities of the peripheral and central nervous systems of rats and humans. These similarities are evident both in terms of behavioral responses to painful conditions and in terms of pain relieving effects of various therapeutic agents (i.e. opiates and nonsteroidal anti-inflammatory drugs) in both species.

Methods

Animal Selection

A statistical power calculator (Massachusetts General Hospital on-line power calculator, http://hedwig.mgh.harvard.edu/sample_size/size.html) was used to determine the appropriate group size to ensure interpretable and reproducible results. Data from previous studies were input into the calculator and the group size was calculated based on a joint compression threshold difference of 68 g with a power of 80% and a standard deviation of 51 g. These parameters resulted in a group size calculation of 10.

A total of 55 rats were treated with CFA to ensure that at least 50 rats (i.e., ten rats for each of five groups) met the inclusion criterion. It has been established that intracapsular injection of CFA into the ankle joint leads to a robust pain state that can be characterized by mechanical hyperalgesia in approximately 90% of rats (that is, 10% of the rats undergoing CFA injection do not meet the study inclusion criterion for mechanical hyperalgesia). Therefore, to ensure that 50 rats meet inclusion criteria, 55 animals were injected with CFA as suggested by the power analysis.

Animal Testing

Following IACUC approval and acclimation, inflammatory arthritis pain was induced in in 55 male, Sprague-Dawley rats by intracapsular injection of 50 μL of 100% complete Freund's adjuvant (CFA) into the tibio-tarsal joint of the left hind leg. Mechanical hyperalgesia was assessed via joint compression thresholds (JCTs), JCTs were determined prior to CFA injection and 14 days post-CFA, prior to study article administration. At that time, 50 animals that met the inclusion criterion were randomly assigned to 5 groups with 10 animals per group (Table 3). To further confirm the validity as a model for arthritic pain, the anti-inflammatory cyclooxygenase-2 inhibitor, celecoxib, was used as an active control.

TABLE 3

Study Design

| | | | Rat: Sprague-Dawley: Male | | | |
|---|---|---|---|---|---|---|
| Test System ID: Species: Breed: Sex | | | Dose | Dose Vol. | | Day of Admin./ |
| Group 4 | Treatment | N | (mg/kg) | (mL/kg) | Route | Frequency |
| 1 | Vehicle (Ethanol: Tween 80: Normal Saline— 1:1:8) | 10 | NA | 5 | IP | Day 0/1x |
| 2 | Compound 1 | 10 | 1 | 5 | IP | Day 0/1x |
| 3 | Compound 1 | 10 | 5 | 5 | IP | Day 0/1x |
| 4 | Compound 1 | 10 | 10 | 5 | IP | Day 0/1x |
| 5 | Celecoxib | 10 | 30 | 5 | PO | Day 0/1x |

Animals were administered a single dose of test or control compound on day 0 (i.e., 14 days after administration of CFA) and thresholds were determined 1, 2, and 4 hours after compound administration. JCTs in test compound-treated animals were compared to those in vehicle-treated animals to determine the analgesic efficacy of the test compound. All behavioral evaluations were performed by a blinded observer.

Mechanical hyperalgesia was measured using a digital Randall-Selitto device (dRS; IITC Life Sciences©; Woodland Hills, Calif.; see Randall, L. O., and J. J. Selitto, "A Method for Measurement of Analgesic Activity on Inflamed Tissue." *Arch. Int. Pharmcodyn.* 11 (1957): 409-19). Animals were allowed to acclimate to the testing room for a minimum of 15 minutes before testing. Animals were placed in a restraint sling that suspended the animal, leaving the hind limbs available for testing. The stimulus was applied to the ankle joint by a blunt tip and pressure was applied gradually over approximately 10 seconds. Joint compression threshold values were recorded at the first observed nocifensive behavior (vocalization, struggle, or withdrawal). One reading per joint was taken at each time point, and a maximum stimulus cutoff of 500 grams was used to prevent injury to the animal. The mean and standard error of the mean (SEM) were determined for ipsilateral and contralateral joints for each treatment group at each time point.

After the pre-dosing baseline assessment on Day 0, only animals that exhibited at least a 25% decrease in joint compression thresholds (JCTs) from pre-injury baseline to pre-dosing baseline were included in the study. All testing was performed in a blinded manner, with all experimenters involved in the study being unaware of the group assignment of any animal they were testing. Animals were assigned to treatment groups based on Day 0 pre-dosing JCTs so that group means of the ipsilateral JCTs were approximately equal. Animals were ranked by ipsilateral JCT and treatments assigned randomly within stratified sub-groups according to the total number of treatment groups in the study. The volume of test or control article injected was 5 mL/kg. The animals were dosed in sequence based on animal number so that the distribution of treatment across a given set of animals was not predictable.

Results

Mechanical Hyperalgesia Development:

To verify the development of mechanical hyperalgesia due to CFA-induced rheumatoid arthritis pain, ipsi lateral and contralateral joint compression thresholds (JCTs) were assessed prior to CFA injection, pre-dosing on Day 0, and 1, 2, and 4 hours post-dosing. Ipsilateral JCTs were compared to contralateral JCTs using an unpaired t-test at each time point as shown in FIG. 4 and Table 4, below. As shown in FIG. 4, Ipsilateral JCTs were significantly lower at all post-CFA time points, indicating persistent mechanical hyperalgesia due to CFA injection.

FIG. 4 shows the mean±standard error of the mean (SEM) values for ipsilateral and contralateral joint compression thresholds (JCTs) in vehicle-treated animals. All animals received 5 mL/kg vehicle ([1 part] Ethanol: [1 part] Tween 80: [8 parts] normal 0.9% Saline) via intraperitoneal injection (n=10). Ipsilateral JCTs were significantly lower at all post-CFA time points, indicating persistent mechanical hyperalgesia due to CFA injection (pre-dose baseline and 1-hour, $p<0.001$; 2-hour and 4-hour, $p<0.0001$ vs. contralateral).

To further verify the development of mechanical hyperalgesia due to CFA injection, a repeated-measured one-way ANOVA was performed on ipsilateral JCTs across all time points tested (Table 4). All post-CFA JCTs were significantly higher than at pre-CFA, indicating significant and persistent mechanical hyperalgesia due to CFA injection.

TABLE 4

Development of Mechanical Hyperalgesia-Statistical Table
Unpaired t-test, two-tailed, Ipsilateral vs. Contralateral

| Time Point | t | Df | p-Value |
|---|---|---|---|
| Pre-Injury Baseline | 1.22 | 18 | 0.240 |
| Pre-Dosing Baseline | 4.11 | 18 | 0.0007 |
| 1 Hour | 4.66 | 18 | 0.0002 |
| 2 Hour | 5.98 | 18 | <0.0001 |
| 4 Hour | 5.56 | 18 | <0.0001 |

Test Article Assessment:

Fourteen days after CFA injection, on Day 0, mechanical hyperalgesia was assessed at the pre-dosing baseline (prior to test and control article administration) and 1, 2, and 4 hours post-dosing with test and control articles. Animals were given an intraperitoneal injection of either vehicle, or Compound 1, or an oral gavage dose of celecoxib. All three doses of Compound 1 (1, 5, and 10 mg/kg) significantly reversed mechanical hyperalgesia at the 2-hour and 4-hour time points, while the 10 mg/kg dose significantly reversed mechanical hyperalgesia at all three time points tested (1, 2, and 4 hours post dose) as shown in FIG. 5.

FIG. 5 shows the mean±SEM for ipsilateral paw compression thresholds following CFA injection in animals treated with either vehicle (5 mL/kg, IP), Compound 1 (1, 5, or 10 mg/kg, intraperitoneal (IP)), or celecoxib (30 mg/kg by mouth (PO)). Ten rats were evaluated in each group. Compound 1 (10 mg/kg) significantly increased paw compression thresholds compared to vehicle at all time points, ($p<0.001$, one-way ANOVA) and the other doses of Compound 1 (1 mg/kg and 5 mg/kg) significantly improved paw compression thresholds at both the 2-hour and 4-hour time points ($p<0.01$, one-way ANOVA). Celecoxib did not significantly improve thresholds at 1-hour but did show improvement compared to vehicle at the 2-hour and 4-hour time points ($p<0.001$, t test).

As shown in FIG. 5, intraperitoneal administration of Compound 1 significantly reversed CFA-induced mechanical hyperalgesia. At 1 mg/kg and 5 mg/kg, Compound 1 significantly increased JCTs at the 2- and 4-Hour time points. At 10 mg/kg, Compound 1 significantly increased JCTs at all three post-dosing time points tested (1-, 2-, and 4-Hour). The reversal in mechanical hyperalgesia was comparable to the active control, celecoxib.

Example 3

Neuropathic Pain Model in Rats

This study evaluated the efficacy of a single intraperitoneal injection of Compound 1 and the comparator, gabapentin, in the spinal nerve ligation (SNL) model for neuropathic pain in the rat. Rats have been used as a reliable animal model for the study of pain due to many similarities of the peripheral and central nervous systems of rats and humans. These similarities are evident both in terms of behavioral responses to painful conditions and in terms of pain relieving effects of various therapeutic agents (i.e. opiates and nonsteroidal anti-inflammatory drugs) in both species. Further, rats are vertebrates, which is necessary when investigating the effects of neuropathic pain.

Methods

Animal Selection

A statistical power calculator (Massachusetts General Hospital on-line power calculator, http://hedwig.mgh.harvard.edu/sample_size/size.html) was used to determine the appropriate group size to ensure interpretable and reproducible results. Data from previous studies were input into the calculator and the group size was calculated based on a threshold difference of 4.5 grams with a power of 80% (mean control=3.42, mean treated=7.92, standard deviation=2.1). These input data resulted in a group size calculation of 10.

A total of 55 rats were used to ensure that at least 50 rats (i.e., ten rats for each of five groups) met the inclusion criteria. It has been established that ligation of the L5 and L6 spinal nerves leads to a robust pain state, characterized by tactile allodynia and mechanical hyperalgesia in approximately 90% of rats (that is, ~10% of the rats undergoing SNL surgery do not meet the study inclusion criteria for mechanical sensitivity). Therefore, to ensure 50 rats met inclusion criteria (as indicated by the power analysis), surgery was performed on 55 animals.

Animal Testing

Following IACUC approval and acclimation, neuropathy was induced in 55 male, Sprague-Dawley rats by surgically ligating the $5^{th}$ and $6^{th}$ lumbar spinal nerves (L5 and L6), a procedure also known as spinal nerve ligation (SNL). Mechanical sensitivity was assessed via paw compression thresholds using a digital Randall-Selitto device. Thresholds were determined prior to surgery and 15 days post-surgery, prior to study article administration. At that time, 50 animals that met the inclusion criteria were assigned to 5 groups with 10 animals per group (Table 5). To further confirm the validity as a model for neuropathic pain, gabapentin was used as an active control.

TABLE 5

Study Design

| | | Rat: Sprague-Dawley: Male | | | |
|---|---|---|---|---|---|
| Test System ID: Species: Breed: Sex | | Dose | Dose Vol. | | Day of Admin./ |
| Group # | Treatment | N | (mg/kg) | (mL/kg) | Route | Frequency |
| 1 | Vehicle (Ethanol: Tween 80: Normal Saline—1:1:8) | 10 | NA | 5 | IP | Day 0/1x |
| 2 | Compound 1 | 10 | 1 | 5 | IP | Day 0/1x |
| 3 | Compound 1 | 10 | 5 | 5 | IP | Day 0/1x |
| 4 | Compound 1 | 10 | 10 | 5 | IP | Day 0/1x |
| 5 | Gabapentin | 10 | 100 | 5 | IP | Day 0/1x |

Animals were administered a single dose of test or control compound on day 0 (i.e., 15 days after SNL) and thresholds were determined 1, 2, and 4 hours after compound administration. Response thresholds in test compound-treated animals were compared to those in vehicle-treated animals to determine the analgesic efficacy of the test compound. All behavioral evaluations were performed by a blinded observer.

Mechanical hyperalgesia was measured using a digital Randall-Selitto device (dRS; IITC Life Sciences©; Woodland Hills, Calif.) (see Randall, L. O., and J. J. Selitto. "A Method for Measurement of Analgesic Activity on Inflamed Tissue." *Arch. Int. Pharmcodyn.* 11 (1957): 409-19). Animals were allowed to acclimate to the testing room for a minimum of 15 minutes before testing. Animals were placed in a restraint sling that suspends the animal, leaving the hind limbs available for testing. The stimulus was applied to the plantar surface of the hind paw by a cone-shaped tip and pressure was applied gradually over approximately 10 seconds. Paw compression threshold values were recorded at the first observed nocifensive behavior (vocalization, struggle, or withdrawal). One reading per paw was taken at each time point, and a maximum stimulus cutoff of 300 grams was used to prevent injury to the animal. The mean and standard error of the mean (SEM) were determined for ipsilateral and contralateral paws for each treatment group at each time point.

After the pre-treatment baseline assessment on day 0, only animals that exhibited at least a 25% decrease in thresholds from pre-injury baseline to pre-dosing baseline OR a 1.5 ratio of contralateral/ipsilateral thresholds were included in the study. All testing was performed in a blinded manner, with all experimenters involved in the study being unaware of the group assignment of any animal they were testing.

Animals were assigned to treatment groups based on Day 0 pre-dosing dRS paw compression thresholds so that group means of the ipsilateral paw compression thresholds were approximately equal. Animals were ranked by ipsilateral paw compression threshold measurement from lowest to highest and treatments assigned randomly within stratified sub-groups according to the total number of treatment groups in the study.

The volume of test or control article injected was 5 mL/kg. The animals were dosed in sequence based on animal number, so that the distribution of treatment across a given set of animals was not predictable.

Results
Hyperalgesia Development:

In order to verify the development of mechanical hyperalgesia due to SNL surgery, ipsilateral and contralateral paw compression thresholds were assessed prior to SNL surgery, post-SNL surgery prior to day 0 dosing, and at 1, 2, and 4 hours post-dosing on day 0. Ipsilateral paw compression thresholds were compared to contralateral paw compression thresholds using an unpaired t-test at each time point. Ipsilateral paw compression thresholds were significantly lower at all post-SNL time points as shown in FIG. 6 and Table 6, indicating persistent mechanical hyperalgesia due to SNL surgery.

FIG. 6 shows the mean±standard error of the mean (SEM) values for ipsilateral and contralateral paw compression thresholds following SNL surgery in vehicle-treated animals. All animals received vehicle ([1 part] Ethanol: [1 part] Tween 80: [8 parts] normal 0.9% Saline—5 mL/kg) via intraperitoneal injection (n=10). Significantly reduced ipsilateral paw compression thresholds were noted at all time points following injury: Pre-dosing baseline ($p<0.001$), 1-hour ($p<0.0001$), 2-hour ($p<0.001$) and 4-hour ($p<0.0001$) vs. contralateral.

To further verify the development of mechanical hyperalgesia due to SNL, a repeated-measured one-way ANOVA was performed on ipsilateral paw compression thresholds (PCTs) across all time points tested (Table 6). All post-SNL PCTs were significantly higher than at pre-SNL, indicating significant and persistent mechanical hyperalgesia due to SNL.

TABLE 6

Development of Hyperalgesia-Statistical Table
Unpaired t-test, two-tailed, Ipsilateral vs. Contralateral

| Time Point | t | Df | p-Value |
|---|---|---|---|
| Pre-Injury Baseline | 0.6803 | 18 | 0.505 |
| Pre-Dosing Baseline | 4.59 | 18 | 0.0002 |
| 1 Hour | 6.542 | 18 | <0.0001 |
| 2 Hour | 4.098 | 18 | 0.0007 |
| 4 Hour | 7.304 | 18 | <0.0001 |

Test Article Assessment:

Fifteen days after SNL surgery, on study day 0, mechanical hyperalgesia was assessed at the pre-dosing baseline (prior to test and control article administration) and 1, 2, and 4 hours post-dosing with test and control articles. Animals were given an intraperitoneal injection of either vehicle ([1 part] ethanol, [1 part] Tween 80, [8 parts] normal 0.9% saline), Compound 1, or Gabapentin. The 1 mg/kg dose of Compound 1 did not significantly reverse mechanical hyperalgesia at any of the time points tested. The 5 mg/kg and 10 mg/kg doses of Compound 1 did not significantly reverse mechanical hyperalgesia at the 1-hour post-dosing time point but did significantly reverse mechanical hyperalgesia at the 2- and 4-hour post-dosing time points as shown in FIG. 7.

FIG. 7 shows the mean±error of the mean (SEM) for ipsilateral paw compression thresholds following SNL surgery in vehicle-, gabapentin-, and Compound 1-treated animals. All animals received vehicle ([1 part] ethanol, [1 part] Tween 80, [8 parts] normal 0.9% saline-5 mL/kg), Compound 1 (1, 5, or 10 mg/kg) or gabapentin (100 mg/kg) via intraperitoneal injection (n=10/group).

The test compound assessed in this study, Compound 1, was administered at doses of 1 mg/kg, 5 mg/kg, and 10 mg/kg. The 1 mg/kg dose did not significantly reverse SNL-induced mechanical hyperalgesia at any time point tested. The 5 mg/kg and 10 mg/kg doses did not significantly reverse SNL-induced mechanical hyperalgesia at the 1-hour post-dosing time point but did significantly reverse SNL-induced mechanical hyperalgesia at the 2-hour ($p<0.05$ versus vehicle by one-way ANOVA) and 4-hour ($p<0.001$ versus vehicle by one-way ANOVA) post-dosing time points. Gabapentin significantly reversed SNL-induced mechanical hyperalgesia at 1, 2, and 4-hours (p<0.01 versus vehicle by t test). The reversal of mechanical hyperalgesia by Compound 1 at 5 mg/kg and 10 mg/kg did not differ significantly from the active control, gabapentin.

Example 4

Bone Cancer Model of Pain in the Rat

In this study, the effect of test article Compound 1 on osteolytic bone cancer pain induced in the MRMT-1 model was studied in female, Sprague-Dawley rats. This study evaluated the efficacy of a single intraperitoneal injection of Compound 1 and the comparator, subcutaneous morphine, in the MRMT-1 cancer cell model of osteolytic cancer pain in the rat. Rats have been used as a reliable animal model for the study of pain due to many similarities of the peripheral and central nervous systems of rats and humans. These similarities are evident both in terms of behavioral responses to painful conditions and in terms of various therapeutic agents (e.g., opioids, non-steroidal anti-inflammatory drugs, anticonvulsants and antidepressants) in both species. Rats are among the best species for determining the predictability of efficacy of therapeutic agents in humans. Further, rats are vertebrate animals which enables the investigation of the effects of post-surgical pain.

Methods

Animal Selection

A statistical power calculator (Massachusetts General Hospital on-line power calculator, http://hedwig.mgh.harvard.edu/sample_size/size.html) was used to determine the appropriate group size based on a threshold difference of 14 percent as measured by weight bearing score (WBS) with a power of 90% and a standard deviation of 9 (parallel study with a quantitative measurements). These parameters and input data from previous studies resulted in a group size calculation of 10 animals per group.

Originally, five experimental groups were proposed as follows: Group 1 (vehicle); Group 2 (1 mg/kg Compound 1); Group 3 (5 mg/kg Compound 1); Group 4 (10 mg/kg Compound 1); and Group 5 (morphine). However, the cancer model was initially successfully induced in only 40 animals, which would have resulted in only eight animals per group. Moreover, due to considerable variability in the vehicle group, at interim evaluation the positive control (morphine) did not significantly reduce pain behaviors at any time point. Accordingly, in order to ensure reproducible results, the experiment was redesigned. A new power analysis was performed yielding a group size of 14 to enable a detection of 11.5 units (percent WBS) with a standard deviation of 9 units at a power of 90%. The IACUC approved an additional 6 animals in each of 3 groups (vehicle (Group 1), Compound 1 [10 mg/kg] (Group 4) and morphine (Group 5). Only 15 of the additional 18 animals developed the condition resulting in successful model development with 13 animals per group.

Animal Testing

Osteolytic bone cancer was produced by an injection of 3000 mammary gland carcinoma cells (MRMT-1) into the intramedullary space of the tibia. Animals received either vehicle or Compound 1 (10 mg/kg) intraperitoneally on Day 0. Morphine (6 mg/kg) served as the positive control for this study and was administered via subcutaneous injection. Bone cancer pain was assessed by measuring hind limb percent weight bearing scores (percent WBS) prior to inoculation (study day −21), and prior to administration (BL), 1, 2, and 4 hours after administration on Day 0.

Hind limb weight bearing scores (WBS) are measured using a Linton Incapacitance Tester (Stoelting Co.©, Wood Dale, Ill.; see Medhurst, S. J., K. Walker, M. Bowes, B. L. Kidd, M. Glatt, M. Muller, M. Hattenberger, J. Vaxelaire, T. O'Reilly, G. Wotherspoon, J. Winter, J. Green, and L. Urban. "A Rat Model of Bone Cancer Pain." *Pain* 96 (2002): 129-40). Animals were allowed to acclimate to the testing room for a minimum of 15 minutes before testing. Animals are placed in an acrylic test chamber. When the animal is in the correct position in the test chamber an evaluation of force was taken, with the evaluation measuring the average force exerted individually by each hind paw over a three second interval. Three evaluations of force per animal are taken at each time point. The percent WBS for the injured leg is calculated for each evaluation of force using the following formula:

$$\% \text{ weight bearing score} = \left[ \frac{\text{weight on left leg}}{(\text{weight on left leg} + \text{weight on right leg})} \right] \times 100$$

The mean of the 3% WBS values is taken as the % WBS for that time point. The mean and standard error of the mean (SEM) are determined for each treatment group at each time point.

Success Criteria

Model creation: Significant decrease in % WBS.

Model sensitivity: Significant reversal of % WBS by morphine.

Inclusion: Only animals that exhibit a post-injury % WBS equal to or less than 40 were included in the study.

Blinding: All testing was performed in a blinded manner, with all experimenters involved in the study being unaware of the group assignment of any animal they were testing.

Group assignment: Animals were assigned to treatment groups based on Day 0 pre-dosing percent WBS so that group means were approximately equal. Animals were ranked by percent WBS from lowest to highest and treatments assigned randomly within stratified sub-groups according to the total number of treatment groups in the study.

Dosing: The volume of test or negative control article injected was 5 mL/kg via intraperitoneal injection or 2 mL/kg via subcutaneous injection for morphine. The animals were dosed in sequence based on animal number, so that the distribution of treatment across a given set of animals was not predictable (Table 7).

TABLE 7

| Study design | | | | | | |
|---|---|---|---|---|---|---|
| Test System ID: Species: Breed: Sex | | | | Rat: Sprague-Dawley, Female | | |
| Group # | Treatment | N | Dose (mg/kg) | Dose Vol. (mL/kg) | Route | Day of Admin./ Frequency |
| 1 | Vehicle | 13 | NA | 5 | IP | Day 0, 1x |
| 2 (not evaluated) | Compound 1 | 8 | 1 | 5 | IP | Day 0, 1x |
| 3 (not evaluated) | Compound 1 | 8 | 5 | 5 | IP | Day 0, 1x |
| 4 | Compound 1 | 13 | 10 | 5 | IP | Day 0, 1x |
| 5 | Morphine | 13 | 6 | 2 | SQ | Day 0, 1x |

Results

To assess the presence of weight bearing asymmetry throughout the pharmacological assessment period, hind limb weight bearing scores from pre-treatment baselines on Day 0 in the vehicle group were compared to the pre-inoculation baseline using an un-paired, two-tailed t-test.

Mean hind limb weight bearing scores pre-dosing on Day 0 (BL) were significantly lower than pre-inoculation baseline as shown in FIG. 8, indicating the presence of significant weight bearing asymmetry, but only at pre-dosing baseline. Variability in the vehicle group at later time points was noted.

FIG. 8 shows the mean±standard error of the mean (SEM) values for percent WBS in vehicle-treated animals during the pharmacologic assessment period. All animals received vehicle (5 mL/kg) via intraperitoneal injection (n=13). Significant asymmetry in weight-bearing was noted at the pre-dosing time point (p<0.0001 vs. pre-injury, unpaired, two-tailed t-test).

Inoculation with MRMT-1 cancer cells produced, once established, a robust and consistent hind limb weight bearing asymmetry demonstrated by significant differences in percent WBS between pre-inoculation and pre-dosing percent WBS in the vehicle group.

Subcutaneous administration of morphine (6 mg/kg) produced a time-dependent reversal of hind limb weight bearing asymmetry at 1 and 2 hours when compared to pre-dosing baseline.

Intraperitoneal administration of Compound 1 (10 mg/kg) produced significant reversal of hind limb weight bearing asymmetry at 4 hours when compared to pre-dosing baseline as shown in FIG. 9.

FIG. 9 shows the mean±standard error of the mean (SEM) values for the weight bearing scores (%) following bone cancer development in vehicle-, morphine-, and Compound 1-treated animals. All animals received vehicle ([1 part] ethanol, [1 part] Tween 80, [8 parts] normal 0.9% saline 5 mL/kg), or Compound 1 (10 mg/kg) via intraperitoneal injection, or morphine (6 mg/kg) subcutaneously (n=13/group).

Morphine produced significant change in the weight-bearing asymmetry compared to vehicle only at 1-hour (p=0.02). Compared to pre-dose baseline, however, morphine significantly improved weight-bearing at 1-hour (p<0.01) and 2-hour time points (p<0.01). Morphine did not produce significant improvement at 4-hours (p=ns). Compound 1 (10 mg/kg) did produce significant improvement in weight-bearing at 4-hours compared to pre-dose BL (p<0.001) (two-tailed t-tests.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of treating pain caused by inflammation or an inflammatory response in a subject in need thereof, the method comprising administering to the subject a therapeutically effective amount of Compound 1:

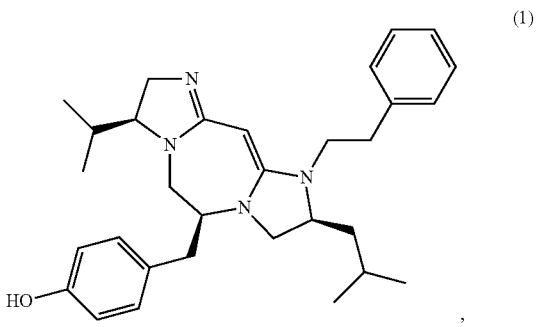 [SMILES: CC(C)C[C@H]1CN2C(=CC3=NC[C@H](C(C)C)N3C[C@@H]2Cc2ccc(O)cc2)N1CCc1ccccc1]

(1)

or a pharmaceutically acceptable salt, tautomer, or isomer thereof, wherein the pain caused by inflammation or inflammatory response is associated with hyperalgesia, arthritis pain, low back pain, neuropathic pain, visceral pain, pain due to cancer, pain due to injury, pain due to cutaneous/subcutaneous or joint inflammation, pain due to back disorders, or neck pain.

2. The method of claim 1, wherein the pain is caused by initiation of the inflammatory response.

3. The method of claim 1, wherein the pain is associated with hyperalgesia.

4. The method of claim 1, wherein the pain is chronic pain or subacute pain.

5. The method of claim 4, wherein the chronic pain is arthritis pain, low back pain, neuropathic pain, visceral pain, pain due to cancer, pain due to injury, pain due to joint inflammation, pain due to back disorders, or neck pain.

6. The method of claim 5, wherein the pain due to cancer is caused by cancer involving intraperitoneal abdominal and pelvic organs or bone cancer or bone metastases.

7. The method of claim 5, wherein the pain due to injury is caused by bone, ligament, or tendon injury.

8. The method of claim 1, wherein Compound 1 reduces pain to a similar degree as a central-nervous system-acting opioid.

9. The method of claim 8, wherein the central-nervous system-acting opioid activates a mu receptor.

10. The method of claim 8, wherein the central-nervous system-acting opioid is morphine.

11. The method of claim 1, wherein administrating Compound 1 does not result in any central-nervous system side effects.

12. The method of claim 11, wherein the central nervous system side-effects are addiction, constipation, sedation, impaired mentation, somnolence, respiratory depression, nausea, dysphoria, or seizures.

13. The method of claim 12, wherein administering Compound 1 does not result in constipation.

14. The method of claim 12, wherein administrating Compound 1 does not result in addiction.

15. The method of claim 1, wherein Compound 1 results in synergistic activation of kappa and delta opioid receptors.

16. The method of claim 15, wherein the synergy results from allosteric modulation of kappa receptors by delta receptor activity.

17. The method of claim 1, wherein administration of Compound 1 is similar or superior to a kappa receptor agonist for treatment of acute pain.

18. The method of claim 1, wherein administration of Compound 1 is similar or superior to a kappa receptor agonist for treatment of hyperalgesia.

19. The method of claim 1, wherein administration of Compound 1 results in reduced urinary output compared to a kappa receptor agonist.

20. A method of preventing pain caused by inflammation or an inflammatory response in a subject in need thereof, the method comprising administering to the subject a therapeutically effective amount of Compound 1:

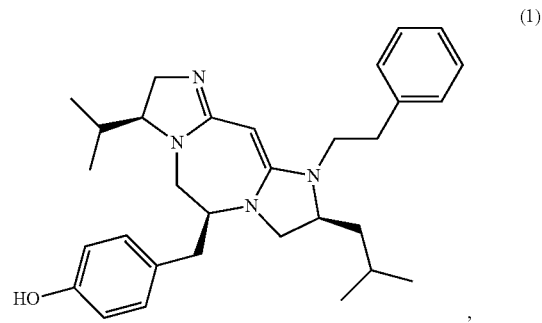 [SMILES: CC(C)C[C@H]1CN2C(=CC3=NC[C@H](C(C)C)N3C[C@@H]2Cc2ccc(O)cc2)N1CCc1ccccc1]

(1)

or a pharmaceutically acceptable salt, tautomer, or isomer thereof, wherein the pain caused by inflammation or inflammatory response is associated with hyperalgesia, arthritis pain, low back pain, neuropathic pain, visceral pain, pain due to cancer, pain due to injury, pain due to cutaneous/subcutaneous or joint inflammation, pain due to back disorders, or neck pain.

* * * * *